(12) United States Patent
Forsell

(10) Patent No.: US 6,470,892 B1
(45) Date of Patent: Oct. 29, 2002

(54) MECHANICAL HEARTBURN AND REFLUX TREATMENT

(75) Inventor: Peter Forsell, Menzingen (CH)

(73) Assignee: Obtech Medical AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/502,074

(22) Filed: Feb. 10, 2000

(51) Int. Cl.$^7$ .................................................. A61F 2/04
(52) U.S. Cl. .................. 128/899; 623/23.65; 623/23.67
(58) Field of Search ............................... 128/897, 898, 128/899; 600/29–32, 37; 606/139–141, 157–158; 623/23.65, 23.67

(56) References Cited

U.S. PATENT DOCUMENTS

| | | | | |
|---|---|---|---|---|
| 3,750,194 A | * | 8/1973 | Summers .................. 600/31 X |
| 3,875,928 A | * | 4/1975 | Angelchik ................... 600/37 |
| 4,246,893 A | * | 1/1981 | Berson ....................... 128/898 |
| 4,271,827 A | | 6/1981 | Angelchik |
| 4,592,355 A | * | 6/1986 | Antebi ....................... 606/144 |
| 4,696,288 A | * | 9/1987 | Kuzmak et al. ............. 128/898 |
| 5,006,106 A | * | 4/1991 | Angelchik .................. 128/898 |
| 5,074,868 A | * | 12/1991 | Kuzmak ..................... 606/157 |
| 5,160,338 A | * | 11/1992 | Vincent ...................... 606/157 |
| 5,226,429 A | * | 7/1993 | Kuzmak ..................... 128/898 |
| 5,316,543 A | * | 5/1994 | Eberbach .................... 128/897 |
| 5,449,368 A | * | 9/1995 | Kuzmak ..................... 606/157 |
| 5,509,888 A | * | 4/1996 | Miller ......................... 600/29 |
| 5,704,893 A | * | 1/1998 | Timm ......................... 600/29 |
| 5,769,877 A | * | 6/1998 | Barreras ..................... 607/61 |
| 5,771,903 A | | 6/1998 | Jakobsson |
| 5,910,149 A | * | 6/1999 | Kuzmak ..................... 606/157 |
| 5,938,669 A | * | 8/1999 | Klaiber et al. .............. 606/157 |
| 5,978,712 A | * | 11/1999 | Suda et al. .................. 607/41 |
| 6,074,341 A | * | 6/2000 | Anderson et al. ............ 600/29 |

FOREIGN PATENT DOCUMENTS

| | | |
|---|---|---|
| WO | WO 00/09047 | 2/2000 |
| WO | WO 00/15158 | 3/2000 |
| WO | WO 01/12078 | 2/2001 |

* cited by examiner

Primary Examiner—Kevin Shaver
Assistant Examiner—Joseph A. Cadugan
(74) Attorney, Agent, or Firm—Nixon & Vanderhye, P.C.

(57) ABSTRACT

A heartburn and reflux disease treatment apparatus includes an adjustable restriction device implanted in a patient and engaging the stomach close to the cardia or engaging the esophagus to form a restricted cross-sectional area of the food passageway in the stomach or esophagus, and a post-operation non-invasive adjustment device for mechanically adjusting the restriction device to change the cross-sectional area of the passageway. By using a wireless remote control the patient can control the adjustment device, whereby the restriction device works like an artificial sphincter.

93 Claims, 16 Drawing Sheets

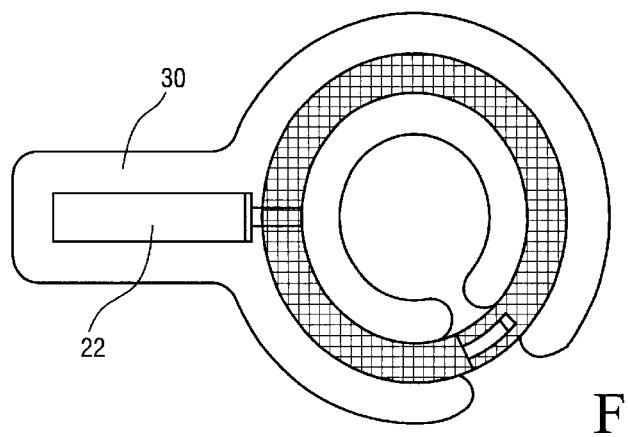
Fig. 4
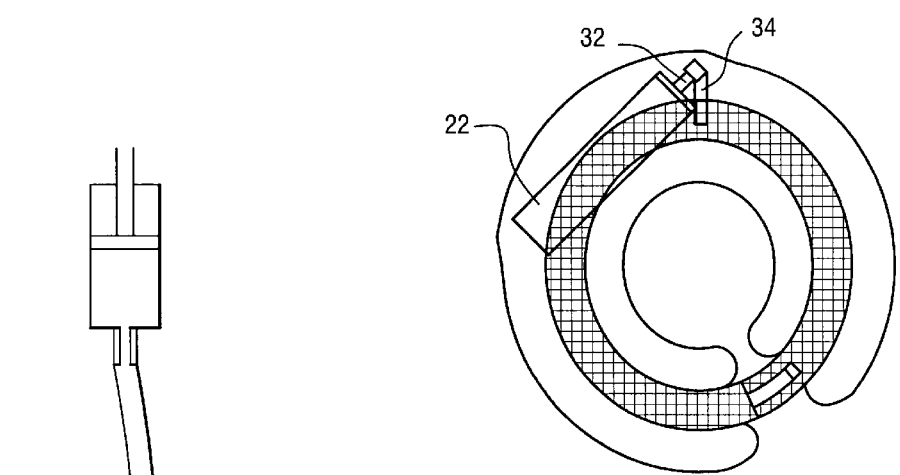
Fig. 5
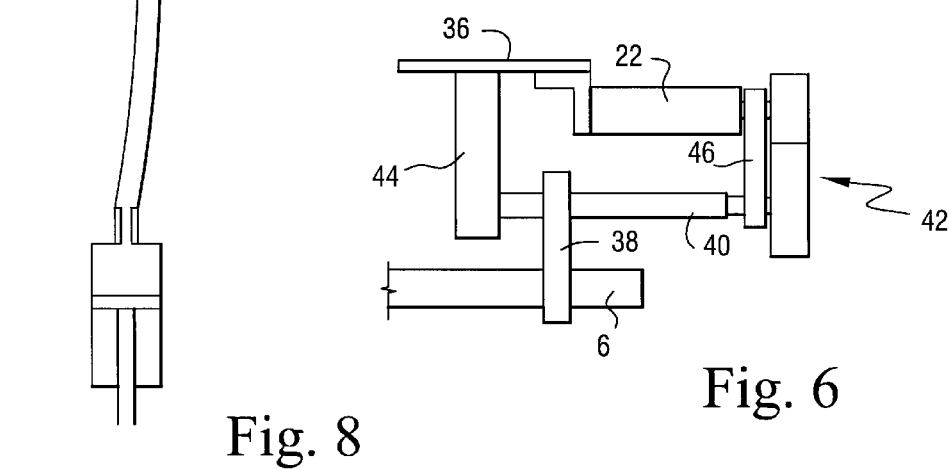
Fig. 8
Fig. 6

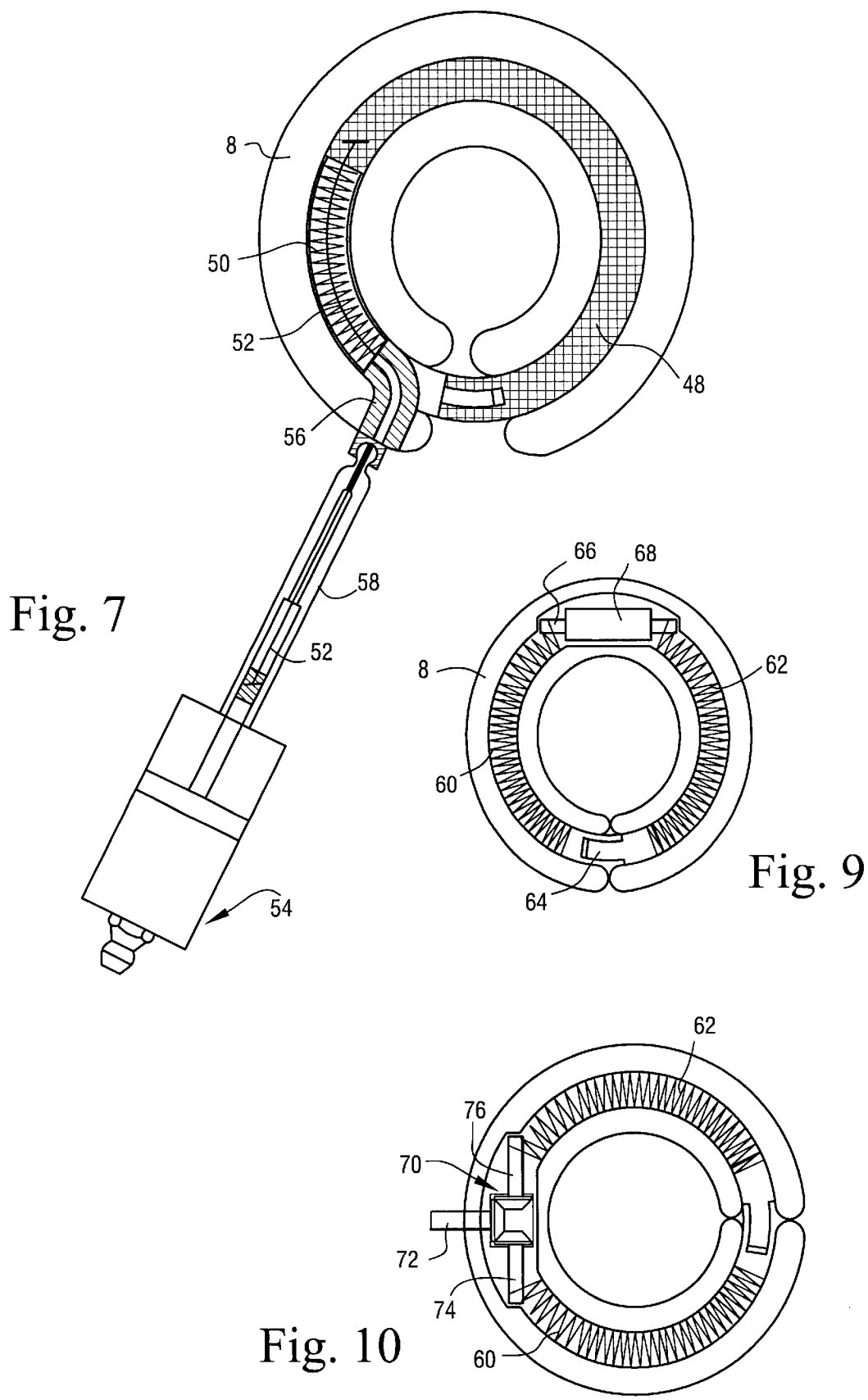

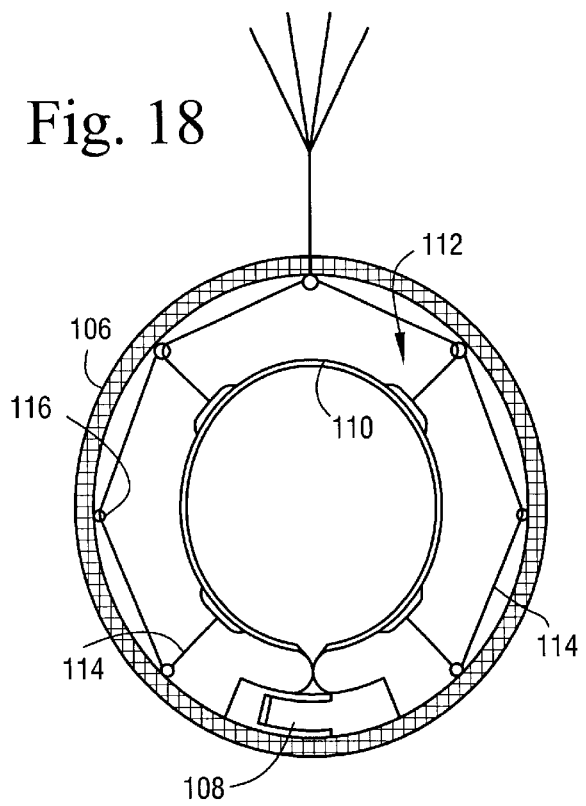
Fig. 18
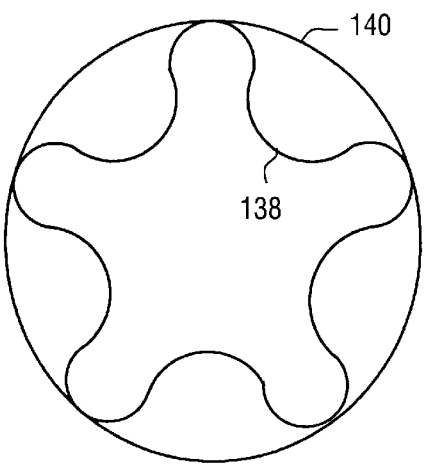
Fig. 20
Fig. 28
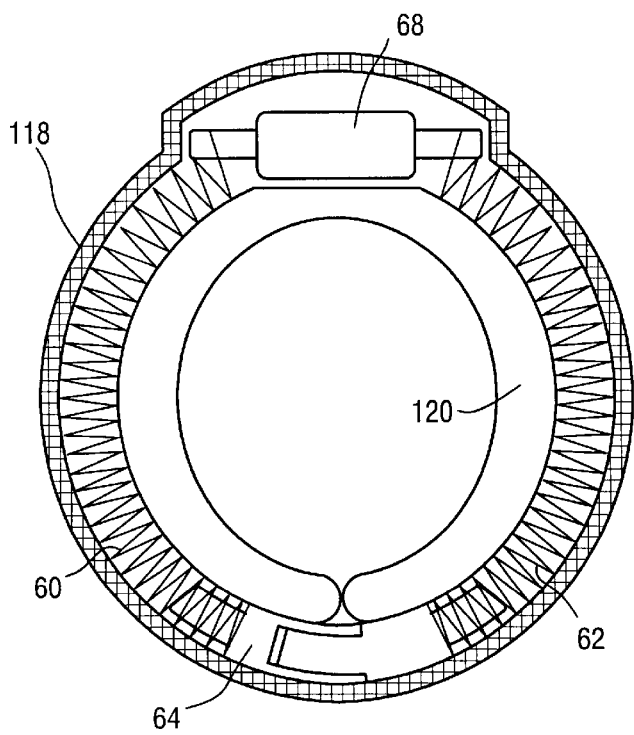
Fig. 19

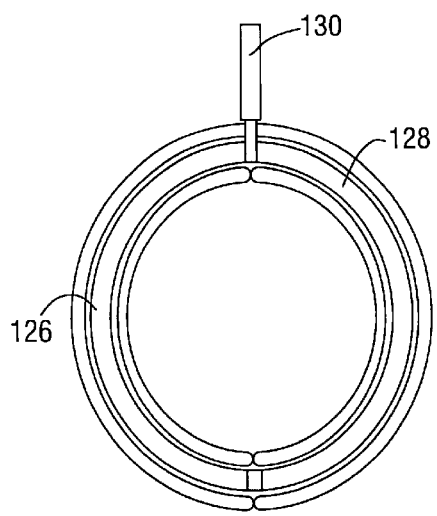
Fig. 21
Fig. 22
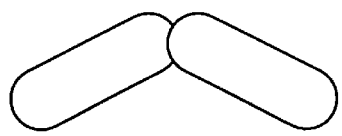
Fig. 23
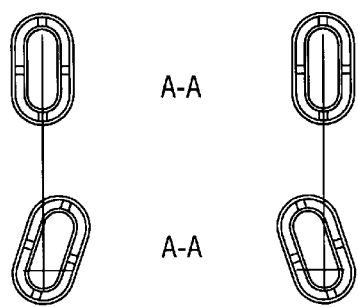
Fig. 26
Fig. 27
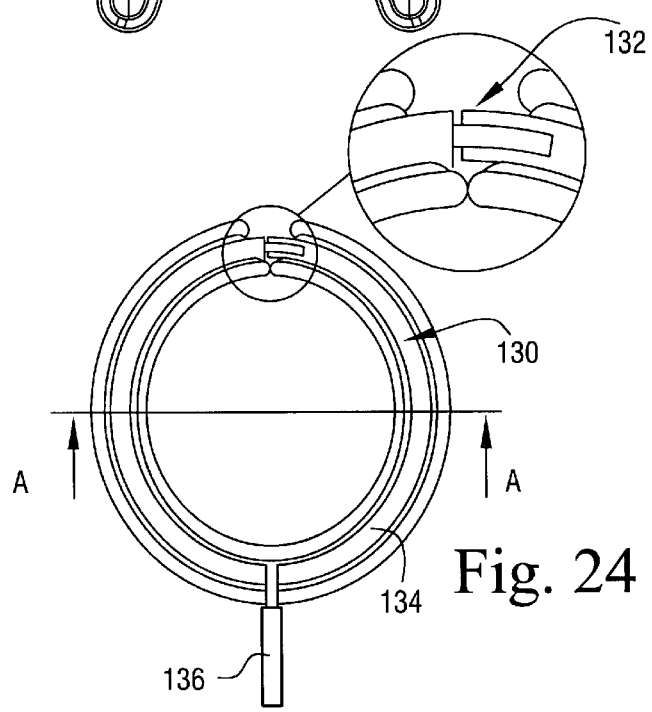
Fig. 25
Fig. 24

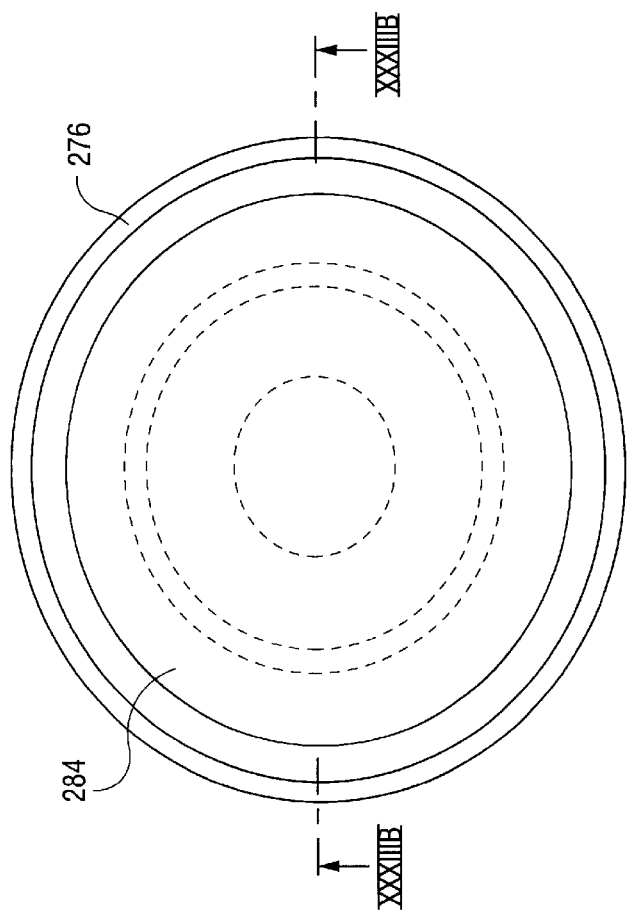
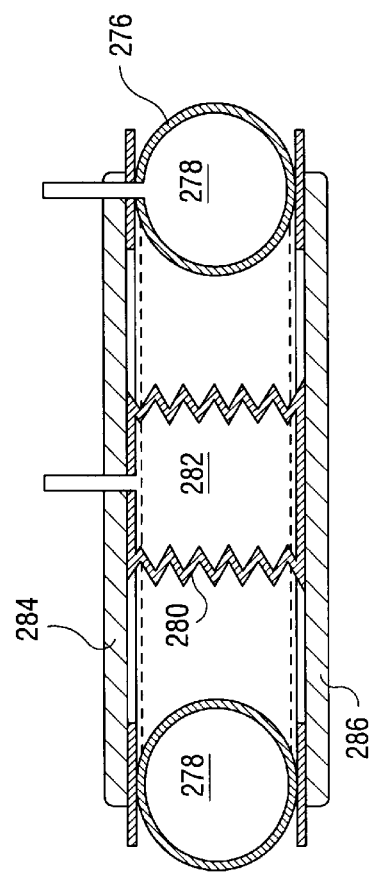
Fig. 33A
Fig. 33B

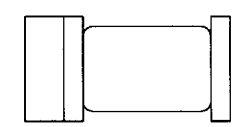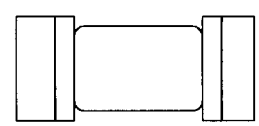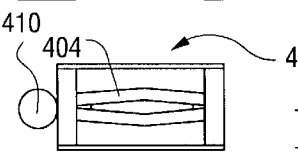
Fig. 36A
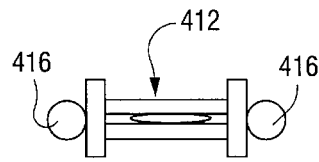
Fig. 37A
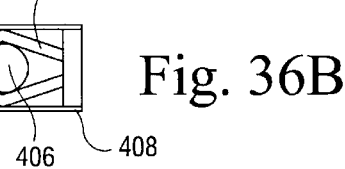
Fig. 36B
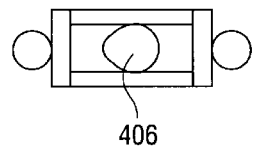
Fig. 37B
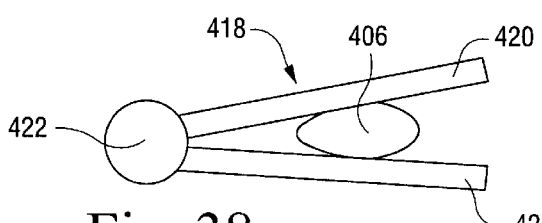
Fig. 38
Fig. 39A
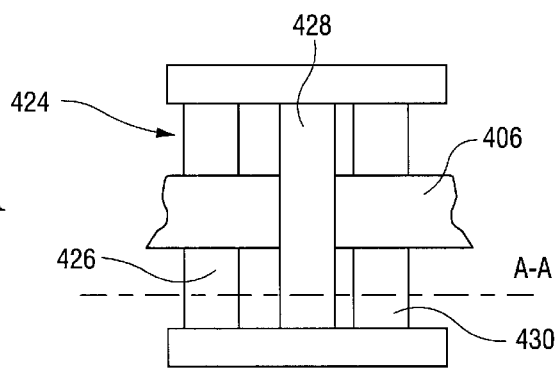
Fig. 39B
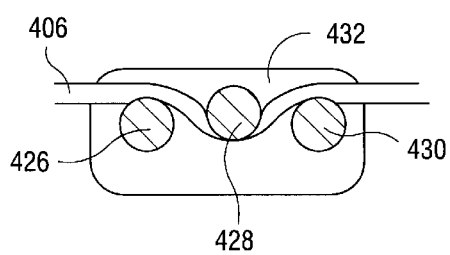
Fig. 39C
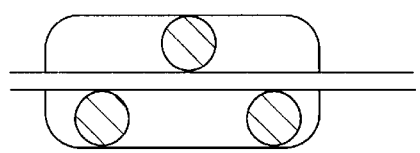

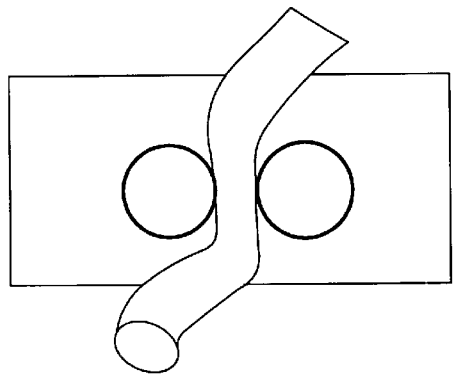 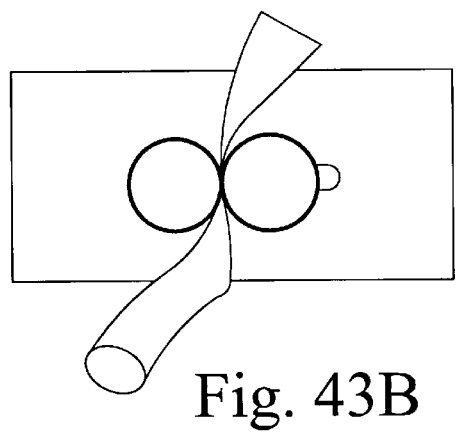
Fig. 43A Fig. 43B
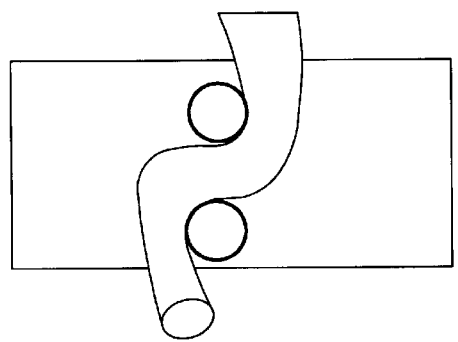 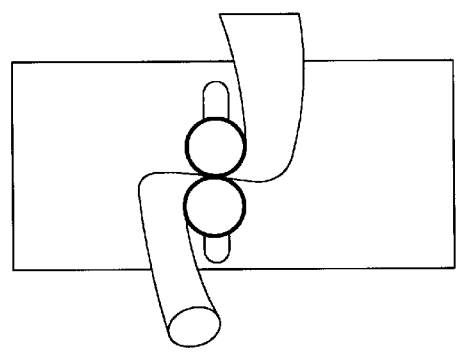
Fig. 44A Fig. 44B

MECHANICAL HEARTBURN AND REFLUX TREATMENT

CROSS REFERENCE TO RELATED APPLICATION

This application incorporates herein by reference the disclosure of provisional application Ser. No. 60/148,345 filed Aug. 12, 1999.

BACKGROUND OF THE INVENTION

The present invention relates to a heartburn and reflux disease treatment apparatus and mehtod. More specifically, the invention relates to a heartburn and reflux disease treatment apparatus and method for surgical application in the abdomen of a patient for forming a restricted food passageway in the esophagus or stomach. The term "patient" includes an animal or a human being.

Chronic heartburn and reflux disease is a widespread medical problem. This is often due to hiatal hernia, i.e. a portion of the stomach immediately below the gastric fundus slides upwardly through the esophageal hiatus. In consequence, stomach acids and foods are regurgitated into the esophagus.

In the late 1970s a prior art prosthesis called Angelchik, according to U.S. Pat. No. 3,875,928, was used to operatively treat heartburn and reflux disease. However, the Angelchik prosthesis had a major disadvantage in that it was not possible to adjust the size of the restriction opening after the operation. A further disadvantage was that the prosthesis did not satisfactorily protect the esophagus and the surrounding area against injuries due to poor shape of the prosthesis. Therefore, operations using the Angelchik prosthesis are no longer practiced.

An operation technique, semi-fundoduplicatio, is currently in use for treating heartburn and reflux disease. A most common operation is Nissen semi-fundoduplicatio, in which one takes the fundus of the stomach and makes a three quarter of a turn around the esophagus and suture between the stomach and esophagus. Although this operation works fairly well it has three main disadvantages. Firstly, most patients treated in accordance to "ad modum Nissen" lose their ability to belch. Secondly, many of these patients get dysphagia, i.e. have difficulties in swallowing after the operation. Thirdly, it is not possible to adjust the food passageway in the esophagus or stomach in any way after the operation. Characteristic for these patients is the variation of their problems over the course of a day. For example, many patients have difficulties during the night when they lie down because of stomach acid leaking up into the esophagus.

The present invention relates to a heartburn and reflux treatment apparatus. More specifically, the invention relates to a heartburn and reflux treatment for surgical application in the abdomen of a patient for forming a food passageway in the esophagus or stomach having a restricted cross-sectional area. The term "patient" includes an animal or a human being.

SUMMARY OF THE INVENTION

The object of the present invention is to provide a new heartburn and reflux disease treatment apparatus which permits post-operation adjustments that are comfortable for the patient.

Accordingly, the present invention provides a heartburn and reflux disease treatment apparatus comprising an adjustable restriction device implanted in the patient and engaging the stomach close to the cardia or esophagus to form a restricted cross-sectional area of the food passageway in the stomach or esophagus, and a post-operation adjustment device which mechanically adjusts the restriction device to change the size of the cross-sectional area. The post-operation adjustment device preferable adjusts the restriction device in a non-invasive manner. As a result, the restriction device performs like an artificial sphincter, which can be adjusted by the patient in connection with every food intake during the day, or possibly only in the morning to open up the food passageway and in the evening to close the food passageway.

The adjustment device may be incorporated in the restriction device as well as being controlled by hydraulic means. The expression "post-operation non-invasive adjustment device" means that the adjustment device is capable of adjusting the restriction device after the operation without the need for invasive measures, such as penetration of the skin for example by injection needles or surgery, or by any other means that penetrate the skin. Though an injection port could be used in embodiments using hydraulic means, the port preferably would be for enabling a single, once and for all, calibration of the amount of liquid contained by the hydraulic means. In this case, the injection port suitably is integrated in the reservoir.)

Generally the implanted restriction device comprises a holding device to prevent the region of the cardia to pass through the esophageal hiatus diaphragmatica. This could be achieved by an enlarged area that should pass the hole in the diaphragmatic muscle where the esophagus passes (a triangular opening surrounded by the crus muscles) or by fixing or holding the region of the cardia in place. The holding device may take the shape of a support member that provides a support for the restriction device upwardly against the diaphragm muscle or sutures or anything formed by human tissue. Alternatively, the restriction device itself could prevent the region of the cardia from sliding up. Means for narrowing the triangular opening could also be provided.

In all applicable embodiments, the restriction device may take any shape and be either hydraulic or non-inflatable. Suitably, the support member is soft.

Preferably, the restriction device comprises an elongated, suitably non-inflatable, restriction member and forming means for forming the restriction member into at least a substantially closed loop around the esophagus or stomach, the loop defining a restriction opening, whereby the adjustment device adjusts the restriction member in the loop to change the size of the restriction opening.

In the various embodiments hereinafter described the restriction member generally forms an at least substantially closed loop. However, the restriction member may take a variety of different shapes, such as the shape of a square, rectangle or ellipse. The restriction member in the substantially closed loop could for example be totally flat, like a belt. The shape of the restriction member may also be changed during use, by rotation or movment in any direction. A physical lumen, such as the passageway in the esophagus, is often easier to restrict by contracting at least two opposite or different side walls of the lumen against each other. Thus, the restriction member may be designed to perform such a contracting effekt of the opposite walls of the esophagus. Either mechanical or hydraulic solutions may be employed to operate the restriction member. Alternatively, the restriction member may comprise an adjustable cuff, a clamp or a roller for bending the esophagus to close or almost close its passageway. Such a cuff, clamp or roller may also be utilized for squeezing the esophagus against human material inside the body of the patient or against implanted structures of the apparatus.

In accordance with a preferred first adjustment principle, the adjustment device adjusts the longitudinal extension of the elongated restriction member in a loop form.

In a preferred embodiment of the invention utilizing the first adjustment principle, the restriction member comprises a main portion and two elongated end portions, and the adjustment device establishes longitudinal relative displacement between the end portions of the restriction member, so that the size of the restriction opening is adjusted. The forming means may comprise any suitable known or conventional device capable of practicing the desired function, such as a spring material forming the elongated restriction member into the loop, so that the restriction opening has a predetermined size, and the adjustment device may adjust the restriction member against the spring action of the spring material. In other words, the restriction member may comprise a spring clip. The spring material may be integrated in the restriction member.

Preferably, the adjustment device comprises a movement transferring member, suitably a drive wheel, in engagement with at least one of the end portions of the restriction member and operable to displace the one end portion relative to the other end portion of the restriction member. The drive wheel may advantageously be in engagement with both of the end portions of the restriction member and be operable to displace said end portions relative to each other. An elongated flexible drive shaft may be operatively connected to the drive wheel, for transferring manual or motor generated power from a location remote from the restriction member. In its simplest embodiment, the drive wheel may comprise a pulley in frictional engagement with the restriction member. As an alternative, a gear rack may be formed on at least one of the end portions of the restriction member and the drive wheel may comprise a gear wheel in mesh with the gear rack. Other suitable known or conventional mechanisms may also or alternatively be used as the adjustment means.

The movement transferring member may alternatively comprise at least one cylinder and a piston, which is movable therein and is connected to one of the end portions of the restriction member, the piston being operable to longitudinally displace the one end portion of the restriction member relative to the other end portion of the restriction member. Alternatively, the movement transferring means may comprise two interconnected cylinders and two pistons in the respective cylinders connected to said end portions, respectively, of the restriction member, the pistons being operable to longitudinally displace the end portions of the restriction member relative to each other. Other known or conventional devices also or alternatively can be used as the movement transferring member.

A motor, which is fixed relative to the main portion of the restriction member and has a rotating drive shaft operatively connected to the movement transferring member, may be positioned relative to the elongated restriction member such that the drive shaft extends transverse thereto. Alternatively, the motor may be positioned relative to the elongated restriction member such that the drive shaft extends substantially tangentially to the loop of the restriction member.

In another embodiment of the invention utilizing the first adjustment principle, the elongated restriction member is longitudinally resilient and the adjustment device comprises a contraction device for longitudinally contracting the resilient restriction member. Preferably, the elongated restriction member comprises a substantially nonresilient main portion and an end portion forming an elongated helical spring, which is contractable by the contraction device. The contraction device may suitably comprise an elongated flexible pulling member connected to the main portion of the restriction member and extending through the helical spring to contract the helical spring against an arresting member, which is fixed relative to the main portion of the restriction member. The pulling member may extend in an elongated tube joined at one end thereof to the arresting member, so that a motor remote from the restriction member may be attached to the other end of the elongated tube and pulls the pulling member through the tube to contract the helical spring.

In yet another embodiment of the invention utilizing the first adjustment principle, the elongated restriction member comprises an elongated helical spring having a free end, and a body to which the spring is nonrotatably secured at its opposite end. The adjustment device rotates the helical spring in one direction to enlarge the coils of the helical spring to longitudinally contract the spring and to rotate the spring in the opposite direction to reduce the size of the coils of the spring to longitudinally extend spring. As a preferred alternative, the restriction member comprises a further elongated helical spring having a free end and nonrotatably secured to the body at its opposite end, and the adjustment device comprises a drive shaft having two opposite end portions connected to the springs, respectively, at their free ends, the helical coils forming left and right hand helices, respectively. The adjustment device may alternatively comprise a gearing having an input shaft and two opposite aligned output shafts connected to the helical springs, respectively, at their free ends, the input shaft being connected to said output shafts so that the output shafts rotate in the opposite directions upon rotation of the input shaft, the helical coils forming the same helices.

In accordance with a second adjustment principle, the adjustment device mechanically adjusts the restriction member so that at least a portion of a radially innermost circumferential confinement surface formed by the restriction member is substantially radially displaced.

In one embodiment of the invention utilizing said second adjustment principle, the restriction member comprises an elongated voltage responsive element forming part of the confinement surface and capable of bending into a bow in response to a voltage applied across the element, the radius of curvature of the bow being adjustable by changing the level of the voltage.

In another embodiment of the invention utilizing said second adjustment principle, the adjustment device changes the diameter of an elastic annular element of the restriction member, which forms the confinement surface. Preferably, the forming means comprises a substantially rigid outer annular element coaxially surrounding the elastic annular element, and the adjustment device comprises means for pulling the elastic annular element radially outwardly towards the outer annular element to expand the elastic annular element. For example, the pulling means may comprise a plurality of threads secured to the elastic annular element along the circumference thereof and running from the elastic annular element via guide members attached to the outer annular element.

In yet another embodiment of the invention utilizing said second adjustment principle, the forming means comprises a substantially rigid outer annular element, and the restriction member comprises an elongated helical spring extending internally along the outer annular element and contacting the latter. The helical spring forms part of the circumferential confinement surface and has a free end. The restriction member further comprises a body to which the spring is nonrotatably secured at its opposite end. The adjustment device rotates the helical spring in one direction to enlarge the coils of the spring to contract the circumferential confinement surface and rotates the spring in the opposite direction to reduce the size of the coils of the spring to expand the circumferential confinement surface. As an alternative, which is preferred, the restriction member comprises two elongated helical springs forming part of the circumferential confinement surface and connected to the body of the restriction member. The adjustment device rotates each spring in one direction to enlarge the coils of the spring to contract the circumferential confinement surface and rotates the spring in the opposite direction to reduce the size of the coils of the spring to expand the circumferential confinement surface.

In accordance with a third adjustment principle, the restriction member comprises at least two separate elements, at least one of which is pivoted so that it may turn in a plane in which the the restriction member extends, and the adjustment device turns the pivoted element to change the size of the restriction opening. Preferably, the restriction member comprises a plurality of separate pivoted elements disposed in series, each pivoted element being turnable in the plane, and the adjustment device turns all of the pivoted elements to change the size of the restriction opening. For example, the pivoted elements may comprise lamellae arranged like the conventional adjustable aperture mechanism of a camera.

In accordance with a fourth adjustment principle, the adjustment device folds at least two foldable frame elements of the restriction member towards each other. Preferably, the foldable frame elements comprise two substantially or partly semi-circular frame elements which are hinged together so that the semi-circular elements are swingable relative to each other from a fully open state in which they form part of a circle to a fully folded state in which they form part of a semi-circle. The same principal may be used with the swingable parts mounted together in one end and not in the other end. Alternatively, the restriction device may comprises at least one preferable two preferable rigid articulated clamping elements positioned on opposite sides of the esophagus or stomach, and the adjustment device turns the clamping elements toward each other to clamp the esophagus or stomach between the clamping elements, thereby decreasing said area, and turns the clamping elements away from each other to release the elements from the esophagus or stomach, thereby increasing said area.

In accordance with a fifth adjustment principle, the adjustment device turns the restriction member around a longitudinal extension thereof, the elongated restriction member being elastic and varying in thickness as seen in a cross-section therethrough. Suitably, the elongated restriction member comprises an elastic belt.

In accordance with a sixth adjustment principle, the adjustment device changes the size of said restriction opening such that the outer circumferential confinement surface of said restriction member is changed.

In accordance with a seventh adjustment principle, the adjustment device changes the size of said restriction opening such that the outer circumferential confinement surface of said restriction member is unchanged.

In accordance with an eighth adjustment principle, the elongated restriction member is flexible, and the adjustment device pulls a first portion of the flexible restriction member from a second portion of the flexible restriction member opposite the first portion in the loop to squeeze the esophagus or stomach between two opposite lengths of the elongated flexible restriction member to decrease the cross-sectional area in the esophagus or stomach and releases the esophagus or stomach from the flexible restriction member to increase the cross-sectional area.

In accordance with a ninth adjustment principle, the restriction device comprises at least two elements on different sides of the esophagus or stomach, and the adjustment device squeezes the esophagus or stomach between the elements to decrease the cross-sectional area in the esophagus or stomach and releases the esophagus or stomach from the elements to increase the cross-sectional area. In all applicable embodiments, the restriction device may have any shape or form and be either hydraulic or non-inflatable.

In accordance with a tenth adjustment principle, the restriction device bends a portion of the esophagus or stomach and comprises at least two displacement members positioned on opposite or different sides of the esophagus or stomach and spaced apart along the food passageway in the esophagus or stomach, wherein the adjustment device moves the displacement members towards the esophagus or stomach to bend the latter, thereby reducing said area, and away from the esophagus or stomach to release them from the displacement members, thereby increasing said area. Suitably, the displacement members comprise rollers. The restriction device may also rotate a portion of the esophagus or stomach. The bending or rotating members may have any shape or form and be either hydraulic or non-inflatable.

The retriction device may comprise two different holders, one placed more distal than the other, forming two at least substantially closed loops. The holders may be rotated in opposite directions to each other. With interconnecting means, for example flexible bands between the different holders, a restriction will occur between the holders when they are rotated.

In all of the above-described embodiments of the invention the adjustment device is conveniently operated by any suitable motor, preferably an electric motor, which may be fixed directly to or be placed in association with the restriction member, or alternatively be located remote from the restriction member, advantageously in the abdomen or subcutaneously. In the latter alternative the motor is advantageously connected to the adjustment device by a flexible power transmission conduit to permit a suitable positioning of the motor in the abdomen of the patient. The motor may be manually activatable, for example by an implanted switch.

In some of the above described embodiments of the invention, however, the adjustment device may conveniently be operable by a hydraulic operation device, which preferably is manually activatable. The hydraulic operation device may advantageously include hydraulic servo means to facilitate manual activation. As an alternative, the hydraulic device may be powered by an electric motor, which may be manually activatable or controlled by remote control means. The components of such a hydraulic operation device may be placed in association with the restriction member and/or be located at a suitable place in the abdomen or subcutaneously.

More specifically, a reservoir may be provided containing a predetermined amount of fluid for supplying the hydraulic operation device with fluid. The reservoir defines a chamber for the predetermined amount of fluid and the hydraulic operation device changes the size of the chamber. The hydraulic operation device may comprise first and second wall portions of the reservoir, which are displaceable relative to each other to change the size of the chamber of the reservoir. The first and second wall portions of the reservoir may be designed to be displaceable relative to each other by manual manipulation thereof, preferably to permit manual pushing, pulling or rotation of any of the wall portions in one direction. Alternatively, the wall portions may be displaceable relative to each other by magnetic means (such as a permanent magnet and magnetic material reed switch, or other known or conventional magnetic devices), hydraulic means or electrical control means such as an electric motor. The magnetic means, hydraulic means, or electrical control means may all be activated by manual manipulation, preferably using a subcutaneously located manually manipulatable device. This control may be indirect, for example via a switch.

The hydraulic operation device may operate the adjustment device with fluid from the reservoir in response to a predetermined first displacement of the first wall portion of the reservoir relative to the second wall portion of the reservoir, to increase the size of the restriction opening, and to operate the adjustment device with fluid from the reservoir in response to a predetermined second displacement of the first wall portion of the reservoir relative to the second wall portion of the reservoir, to decrease the size of the restriction opening. In this embodiment, no pump is used, only the volume of the reservoir is varied. This is of great advantage compared to the solution described below when a pump is used to pump fluid between the reservoir and the adjustment device because there is no need for a non-return valve and it is still possible to have fluid going both to and from the reservoir.

As an alternative, the hydraulic operation device may comprise an activatable pump for pumping fluid between the reservoir and the adjustment device. The pump may pump fluid both to and away from the adjustment device, or hydraulic means controlling the adjustment device. A mechanical manual solution is proposed in which it is possible to pump in both directions just by pushing an activating member in one direction. Another alternative is a pump pumping in only one direction and an adjustable valve to change the direction of fluid to either increase or decrease the amount of fluid in the reservoir. This valve may be manipulated manually, mechanically, electrically, magnetically, or hydraulically. Any kind of motor could of course be used for all the different operations as well as wireless remote solutions. The pump may comprise a first activation member for activating the pump to pump fluid from the reservoir to the adjustment means and a second activation member for activating the pump to pump fluid from the adjustment device to the reservoir. The activation members may be operable by manual manipulation, preferably to permit manual pushing, pulling or rotating thereof in one direction. Suitably, at least one of the activation members is adapted to operate when subjected to an external pressure exceeding a predetermined magnitude.

Alternatively, at least one of the first and second activating members may be operable by magnetic means, hydraulic means or electrical control means such as an electric motor. The magnetic means, hydraulic means, or electrical control means may all be activated by manual manipulating means preferably located subcutaneously. This activation may be indirect, for example via a switch.

Advantageously, especially when manual manipulation means are used, a servo system could be used. With servo means less force is needed for controlling the adjustment device. Hydraulic means is preferably used with servo means. One example is a closed system that controls another closed system in which the hydraulic devices of the adjustment device is incorporated. Minor changes in the amount of fluid in a reservoir of the first system could then lead to major changes in the amount of fluid in a reservoir in the second system. In consequence, the change of volume in the reservoir of the second system affects the hydraulic device of the adjustment device, which is incorporated in the second closed system. The great advantage of this servo system is that the larger volume system could be placed inside the abdomen where there is more space and still would be possible to use manual manipulation means of the smaller system subcutaneously. The servo reservoir could control the reservoir of the larger volume. The servo reservoir could be controlled directly or indirectly by a fluid supply means. The fluid supply means may be a small reservoir, which may be placed subcutaneously and may be activated by manual manipulation means controlling the servo reservoir.

Preferably, the servo means comprises hydraulic means and a servo reservoir and eventually a fluid supply reservoir. Both reservoirs define a chamber containing servo fluid, and the hydraulic means comprises first and second wall portions of the servo reservoir, which are displaceable relative to each other to change the size of the chamber of the servo reservoir. The hydralic means may control the adjustment device indirectly, e.g. via an increased amount of fluid in the servo reservoir, in response to a predetermined first displacement of the first wall portion of any of the reservoirs relative to the second wall portion of the reservoir to decrease the size of the restriction opening, and to control the adjustment device in response to a second displacement of the first wall portion of any reservoir relative to the second wall portion, to indirectly increase the size of the restriction opening. The wall portions of the reservoirs may be designed to be displaceable relative to each other by manual manipulation thereof or be displaceable relative to each other by manually pushing, pulling or rotating any of the wall portions of the reservoir in one direction. Alternatively, the wall portions of the servo reservoir may be displaceable relative to each other by magnetic means, hydraulic means or electric control means including an electric motor.

The magnetic means, hydraulic means, or electrical control means may all be activated by manually manipulated means preferably located subcutaneously. This control may be indirect for example via a switch.

Even in the broadest embodiment of the invention the adjustment device may comprise a servo means. The servo means may comprise a hydraulic operation means, an electrical control means, a magnetic means, mechanical means or a manual manipulation means. The hydraulic operation means, electrical control means, mechanical means or magnetic means may be activated by manual manipulating means. Using a servo system will save the use of force when adjusting the adjustment device which may be of importance in many applications, for example when a battery cannot put out enough current although the total energy in the battery is more than enough to power the system.

The hydraulic fluid used by the operation device in any of the above embodiments may be of a kind that changes viscosity when it is exposed to energy different from thermal energy. For example, the viscosity of the hydraulic fluid may change when the fluid is exposed to electric energy. It should be understood that the word fluid also could incorporate gas or air in all applications.

All solutions may be controlled by a wireless remote control for non-invasively controlling the adjustment device. The remote control may advantageously be capable of obtaining information on the size of the restriction opening or other information related to the implanted components of the apparatus and to command the adjustment device to adjust the restriction member in response to obtained information. With the remote control the apparatus of the invention is conveniently controlled to adjust the implanted restriction device, which controls the cross-sectional area of the food passageway and wherein the restriction device is operable to open and close the food passageway. The restriction device may steplessly controls the cross-sectional area of the food passageway.

The apparatus according may further comprise a pressure sensor for directly or indirectly sensing the pressure against the restriction device and the control device may control the restriction device in response to signals from the pressure sensor. The post-operation adjustment device preferable non-invasively adjusts the restriction device to change the size of the cross-sectional area. The pressure sensor may be any suitable known or conventional pressure sensor such as shown in U.S. Pat. Nos. 5,540,731, 4,846,181, 4,738,267, 4,571,749, 4,407,296 or 3,939,823; or an NPC-102 Medical Angioplasty Sensor.

The apparatus may further comprise an implanted energy transfer device for transferring wireless energy directly or indirectly into kinetic energy for operation of the restriction device.

The remote control permits adjustment of the implanted restriction device any time after the operation, so that the patient may get rid of problems with belching, swallowing etc. The patient can conveniently open up the restriction opening somewhat more when eating and close the restriction opening at night, when going to bed. This new adjustment procedure available to a patient provided with the apparatus of the invention is a great advantage compared to the prior art.

The remote control comprises means for wireless transfer of energy from outside the patient's body to energy consuming implantable components of the device. A motor may suitably be implanted in the patient for operating the adjustment device and the means for wireless transfer of energy may directly power the motor with transferred energy. The energy transferred by the means for transfer of energy may comprise any kind of signals including wave signals, an electric field or a magnetic field.

The wireless remote control comprises an external signal transmitter and/or receiver and an implanted signal receiver and/or transmitter. For example, the signal transmitter and signal receiver(transceivers may be used) may transmit and receive a signal in the form of digital pulses, which may comprise a magnetic or electric field. Alternatively, which is preferred, the signal transmitter and signal receiver may transmit and receive a signal, which comprises an electromagnetic wave signal, a sound wave signal or a carrier wave signal for remote control signals. The receiver may comprise a control unit for controlling the adjustment device in response to a control signal from the signal transmitter.

The apparatus of the invention may further comprise an implanted energizer unit for providing energy to implanted energy consuming components of the apparatus, such as electronic circuits and/or a motor for operating the adjustment device. The control unit may power such an implanted motor with energy provided by the energizer unit in response to a control signal received from the signal transmitter. Any known or conventional signal transmitting or signal receiving device that is suitable for use with a human or mammal patient may be provided as the signal transmitter or signal receiver. The control signal may comprise an electromagnetic wave signal, such as an infrared light signal, a visible light signal, a laser light signal, a micro wave signal, or a sound wave signal, such as an ultrasonic wave signal or an infrasonic wave signal, or any other type of wave signals. The control signal may also comprise electric or magnetic fields, or pulses. All of the above-mentioned signals may comprise digital signals. The control signal may be carried by a carrier signal, which may be the same as the wireless energy signal. Preferably, a digital control signal may be carried by an electromagnetic wave signal. The carrier signal or control signal may be amplitude or frequency modulated.

The motor may be any type of motor, such as a pneumatic, hydraulic or electric motor and the energizer unit may power the motor with pressurized gas or liquid, or electric energy, depending on the type of motor. Where the motor is an electric motor, it may power pneumatic or hydraulic equipment.

The energizer unit may comprise a power supply and the control unit may power the motor with energy from the power supply. Preferably, the power supply is an electric power supply, such as a battery, and the motor is an electric motor. In this case, the battery also continuously powers at least a part of the circuitry of the signal receiver in a standby mode between the adjustment operations, in order to keep the signal receiver prepared for receiving signals transmitted from the signal transmitter.

The energizer unit may transfer energy from the signals, as they are transmitted to the signal receiver, into electric energy for powering the implanted electronic components. For example, the energizer unit may transfer the energy from the signals into a direct or alternating current.

In case there is an implanted electric motor for operating the adjustment device the energizer unit may also power the motor with the transferred energy. Advantageously, the control unit directly powers the electric motor with electric energy, as the energizer unit transfers the signal energy into the electric energy. This embodiment is particularly simple and does not require any recurrent invasive measures for exchanging empty power supplies, such as batteries, that is required in the first embodiment described above.

For adjustment devices of the type that require more, but still relatively low, power for their operation, the energizer unit may comprise a rechargeable electric power supply for storing the electric energy obtained and the control unit may power the electric motor with energy from the rechargeable electric power supply in response to a control signal received from the signal transmitter. In an initial charging step the rechargeable power supply can be charged over a relatively long time (e.g. a few seconds up to a half hour) without powering the electric motor. In a following operating step, when the power supply has been charged with sufficient energy, the control unit powers the electric motor with energy from the charged power supply to operate the adjustment device, so that a desired change of the cross-sectional area of the food passageway is achieved. If the capacity of the power supply is insignificant to achieve the necessary adjustment in one single operating step, the above steps may conveniently be repeated until the desired adjustment is achieved.

The electric power supply suitably comprises an inexpensive simple capacitor. In this case, the electric motor may be a stepping motor. In all cases the motor may preferable be able to perform a reversing function.

The signal transmitter may transmit an electromagnetic control signal and the energizer unit may draw radiant energy from the electromagnetic wave signal, as the latter is transmitted to the signal receiver, and may transfer the radiant energy into electric energy. Alternatively, the energizer unit may comprise a battery, an electrically operable switch for connecting the battery to the signal receiver in an on mode when the switch is powered and for keeping the battery disconnected from the signal receiver in a standby mode when the switch is unpowered, and a rechargeable electric power supply for powering the switch. The control unit may power the electric motor with energy from the battery in response to a control signal received from the signal transmitter, when the switch is in its on mode. Advantageously, the energizer unit may transfer wave energy from the control signal, as the latter is transmitted to the signal receiver, into a current for charging the rechargeable electric power supply, which suitably is a capacitor. Energy from the power supply is then used to change the switch from off (standby mode) to on. This embodiment is suited for adjustment devices of the type that require relatively high power for their operation and has the advantage that the electronic circuitry of the signal receiver does not have to be powered by the battery between adjustments. As a result, the life-time of the battery can be significantly prolonged. The switch may be switched with magnetic, manual or electric energy.

As an example, the signal transmitter may transmit an electromagnetic wave signal and the energizer unit may draw radiant energy from the electromagnetic wave signal, as the latter is transmitted to the signal receiver, and may transfer the radiant energy into electric current. The energizer unit suitably comprises a coil of the signal receiver for inducing an alternating current as the electromagnetic wave signal is transmitted through the coil and a rectifier for rectifying the alternating current. The rectified current is used for charging the rechargeable power source.

Alternatively, the signal transmitter and receiver may solely be used for control signals and a further pair of signal transmitter and receiver may be provided for transferring signal energy to implanted components. By such a double system of signal transmitters and receivers the advantage is obtained that the two systems can be designed optimally for their respective purposes, namely to transmit control signals and to transfer energy from signals. Accordingly, the apparatus may further comprise an external energy transmitter for transmitting wireless energy, wherein the energizer unit comprises a battery and an operable switch for connecting the battery to the signal receiver in an on mode when the switch is powered and to keep the battery disconnected from the signal receiver in a standby mode when the switch is unpowered, the external energy transmitter for powering said switch. Suitably, the energy transmitter may directly power the switch with the wireless energy to switch into the on mode. As should be realized by a skilled person, in many of the above-described embodiments of the invention the adjustment device may be operated by control means or manual manipulation means implanted under the skin of the patient, such as a pump, an electrical switch or a mechanical movement transferring means. In the manual embodiment it is not necessary to use a motor for operating the adjustment device.

In embodiments including hydraulic transmission means, an injection port connected to the hydraulic means may be provided for enabling, normally single, once-and-for-all, calibration of the amount of fluid in the hydraulic system.

In all applications a motor may be operatively connected to the adjustment device and wherein the control of the motor may comprise a reversing device implanted in the patient for reversing the motor. Where the restriction device is capable of performing a reversible function, the reversing device may also reverse the function performed by the restriction device.

In all applications the adjustment device preferable adjusts the restriction device in a non-manual manner without touching the skin of the patient.

The invention also comprises a method for treating heartburn and reflux disease, comprising(a) surgically implanting in the abdomen of a patient suffering from heartburn and reflux disease an adjustable restriction device which forms a food passageway having a restricted cross-sectional area in the esophagus or in the stomach close to the cardia, and (b) when necessary for the patient's health or desired progress, in a non-invasive procedure mechanically adjusting the restriction device to change the size of the cross-sectonal area of the food passageway.

The adjustment device may in all cases be mechanically operated and/or operated in a non-manual manner and be energised by the provision of a source of energy from which energy is released by control means from outside the patient's body to energise the adjustment and/or restriction device.

The invention also provides a surgical method for laparascopically implanting an adjustable restriction device of a heartburn and reflux disease treatment apparatus for forming a food passageway having a restricted cross-sectional area in the esophagus or stomach immediately close to the cardia, the method comprising: (a) Insufflating the abdomen of a patient to form a pneumoperitoneum. (b) Introducing at least one laparascopic trocar into the abdomen. (c) Using a dissecting tool inserted through the laparascopic trocar, dissecting the region of the esophagus or stomach adjacent or above the bursa omentalis. And (d) introducing the restriction device in the abdomen and applying the device on the esophagus or stomach. This method may further comprise after (a)–(d), (e) post-operatively adjusting the restriction device in a non-invasive procedure to change the cross-sectional area of the food passageway.

It is the primary object of the present invention to provide an advantageously yet relatively simple apparatus and method for treating heartburn and reflux disease in a substantially non-invasive manner after initial surgical implantation of a restriction device. This and other objects will become clear from the detailed description and from the appended claims.

BRIEF DESCRIPTION OF THE DRAWINGS

FIGS. 4 and 5 schematically show two alternative designs of the embodiment of FIG. 1;

FIG. 6 schematically illustrates a motor arrangement for the design according to FIG. 5;

FIG. 7 is a schematic sectional view of a second embodiment of the apparatus in accordance with the invention;

FIG. 8 schematically illustrates a hydraulic transmission conduit for the embodiment of FIG. 7;

FIG. 9 is a schematic sectional view of a third embodiment of the apparatus in accordance with the invention;

FIG. 10 is a modification of the embodiment of FIG. 9;

FIGS. 18 to 21 are schematic sectional views of a sixth, seventh, eighth and ninth embodiments, respectively, of the apparatus in accordance with the invention;

FIGS. 22 and 23 illustrate a fully open and a reduced restriction opening, respectively, of the embodiment of FIG. 21;

FIG. 24 is a schematic view of a tenth embodiment of the apparatus in accordance with the invention;

FIG. 25 is an enlarged detail of the embodiment of FIG. 24;

FIGS. 26 and 27 illustrate a fully open and a reduced restriction opening, respectively, of the embodiment of FIG. 24;

FIG. 28 schematically illustrates a cushion arrangement for protecting the stomach or esophagus of the patient;

FIG. 33A is a front view of a hydraulic, pneumatic or mechanical servo system in accordance with a particular embodiment of the principal embodiment shown in FIG. 29D;

FIG. 33B is a cross-sectional view taken along line VB—VB of FIG. 33A;

FIGS. 36A and 36B are schematic views of an eleventh embodiment of the apparatus in accordance with the invention;

FIGS. 37A and 37B are schematic views of a twelfth embodiment of the apparatus in accordance with the invention;

FIG. 38 is a schematic view of a thirteenth embodiment of the apparatus in accordance with the invention;

FIGS. 39A, 39B and 39C are a schematic front view and schematic sectional views, respectively, of a fourteenth embodiment of the apparatus in accordance with the invention;

FIGS. 40A through 44B are five modifications of the embodiment of FIGS. 39A–39C.

DETAILED DESCRIPTION OF THE DRAWINGS

Figures 1, 2, 3:
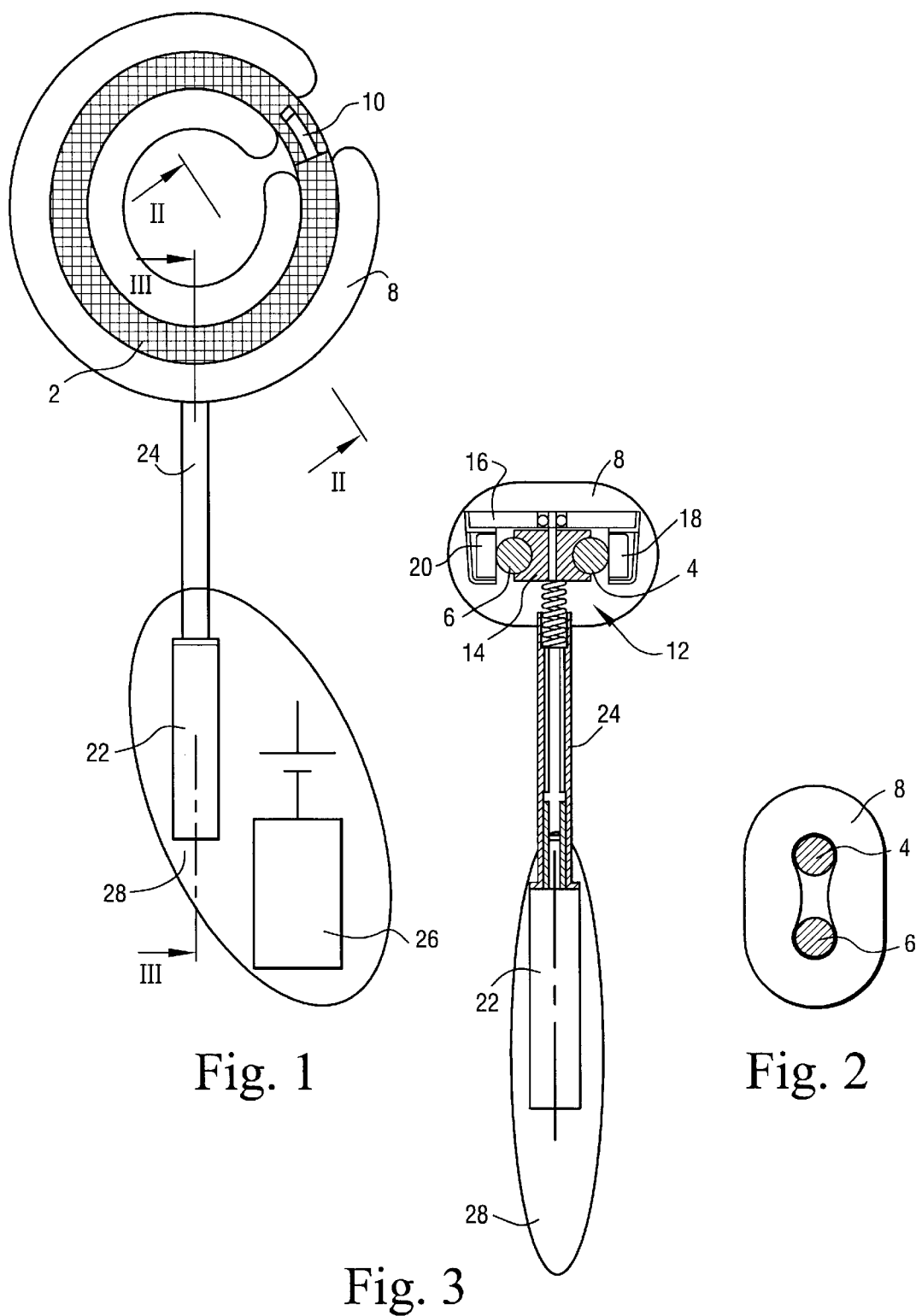
FIG. 1 is a schematic sectional view of a preferred first embodiment of the heartburn and reflux disease treatment apparatus in accordance with the invention.
FIGS. 2 and 3 are cross-sectional views taken along the lines II—II and III—III, respectively, of FIG. 1.
Figure 11:
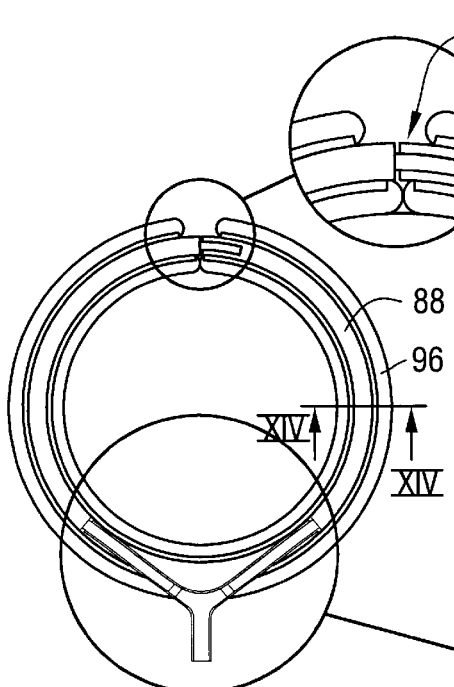
FIG. 11 is a schematic view of a fourth embodiment of the apparatus in accordance with the invention.
Figure 13:
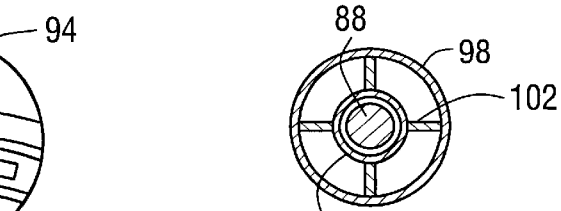
FIGS. 12 and 13 are enlarged details of the embodiment of FIG. 11.

Referring to the drawing figures, like reference numerals designate identical or corresponding elements throughout the several figures.

FIGS. 1–3 show a preferred embodiment of the heartburn and reflux disease treatment apparatus of the invention comprising a restriction device having an elongated restriction member in the form of a circular resilient core 2 with two overlapping end portions 4,6. The core 2 defines a substantially circular restriction opening and is enclosed in an elastic soft hose 8 except at a releasable and lockable joint 10 of the core 2, which when released enables application of the core 2 with its hose 8 around the esophagus or stomach of a patient. The materials of all of these elements are bio-compatible so that the patient's body will not reject them. A post-operation mechanical adjustment device 12 for mechanically adjusting the longitudinal extension of the core 2 to change the size of the restriction opening comprises a drive wheel 14 in frictional engagement with the overlapping end portions 4,6 of the core 2. The drive wheel 14 is journalled on a holder 16 placed in the hose 8 and provided with two counter pressure rollers 18,20 pressing the respective end portions 4,6 of the core 2 against the drive wheel 14 to increase the frictional engagement therebetween. An electric motor 22 is connected to the drive wheel 14 via a long flexible drive shaft 24 and is moulded together with a remote controlled power supply unit 26 in a body 28 of silicone rubber. The length of the flexible drive shaft 34 is selected so that the body 28 can be placed in a desired position in the patient's body, suitably in the abdomen.

If some time after the operation the patient needs an adjustment of the restriction opening of the core 2, the power supply unit 26 is controlled to power the electric motor 22 either to turn the drive wheel 14 in one direction to reduce the diameter of the core 2 or to turn the drive wheel 14 in the opposite direction to increase the diameter of the core 2.

Alternatively, a rack gear may be formed on one of the end portions 4,6 of the core 2 and the drive wheel 14 may be replaced by a drive gear wheel connected to the other end portion of the core 2 and in mesh with the rack gear.

FIG. 4 shows an embodiment of the invention which is identical to the embodiment of FIGS. 1–3, except that the motor 22 is encapsulated in a lateral protrusion 30 of the hose 8 so that it is fixed to the core 2 and has a short drive shaft 32 onto which the drive wheel 14 is mounted, the motor 22 being positioned relative to the circular core 2 such that the drive shaft 32 extends radially thereto.

FIG. 5 shows an embodiment of the invention which likewise is identical to the embodiment of FIGS. 1–3, except that the motor 22 is encapsulated in the hose 8 so that it is fixed to the core 2 and has a short drive shaft 32, the motor 22 being positioned relative to the core 2 such that the drive shaft 32 extends substantially tangentially to the circular core 2. There is an angular gearing 34 connecting the drive shaft 32 to the drive wheel 14.

FIG. 6 shows a suitable arrangement for the motor 22 in the embodiment of FIG. 5, comprising a first clamping member 36 secured to one end portion of the core 2 and a second clamping member 38 secured to the other end portion 6 of the core 2. The motor 22 is secured to the first clamping member 36 and is operatively connected to a worm 40 via a gear transmission 42. The worm 40 is journalled at its opposite ends on holders 44 and 46, which are rigidly secured to the clamping member 36 and the motor 22, respectively. The second clamping member 38 has a pinion in mesh with the worm 40. When the motor 22 is powered the worm 40 rotates and will thereby pull the end portion 6 of the core 2 in one or the opposite longitudinal direction, so that the diameter of the substantially circular core 2 is either increased or decreased.

FIG. 7 shows an embodiment of the invention in which the elongated restriction member comprises a core 48 and a helical spring 50. A spring contracting means in the form of a flexible pulling member 52, i.e. a string, wire or cable, is connected to the core 48 at one end thereof and extends through the helical spring 50. A hydralic motor in the form of a cylinder/piston unit 54 is adapted to pull the flexible pulling member 52 to contract the helical spring 50 against an arresting member 56, which is fixed relative to the core 48. A tube 58 hinged to the arresting member 56 extends between the cylinder/piston unit 54 and the arresting member 56, the flexible pulling member 52 running through the tube 58 and being connected to the piston of the cylinder/piston unit 54. FIG. 8 shows a similar embodiment in which a hydraulic transmission conduit 59 is provided between two piston-cylinder assemblies 54, for use as the hydraulic motor/device in FIG. 7.

FIG. 9 shows an embodiment of the invention in which the restriction member comprises two elongated helical springs 60 and 62 having free ends, and a body 64 to which the springs 60,62 are nonrotatably secured at their opposite ends. The body 64 comprises two separate parts secured to opposite end portions of the enclosing elastic hose 8 and is designed with a releasable and lockable joint between the separate parts. An adjustment device in the form of a drive shaft 66 has two opposite end portions connected to the helical springs 60,62, respectively, at their free ends. The coils of the springs 60,62 form left and right hand helices, respectively. A motor 68 is adapted to rotate the drive shaft 66 in one direction to enlarge the coils of the helical springs 60,62 to longitudinally contract the springs 60,62 and to rotate the drive shaft 66 in the opposite direction to reduce the size of the coils of the springs 60,62 to longitudinally extend the springs 60,62. Thus, the elongated helical springs 60,62 defines a restriction opening, the size of which is increased when the springs 60,62 are extended and decreased when the springs 60,62 are contracted.

FIG. 10 shows an embodiment according to the invention which is identical to the embodiment of FIG. 9, except that the adjustment decice comprises a gearing having an input shaft 72 and two opposite aligned output shafts 74 and 76 connected to the helical springs 60 and 62, respectively, at their free ends. The input shaft 72 is connected to the output shafts 74,76 such that they rotate at opposite directions upon rotation of the input shaft 72. The coils of the springs 60,62 form the same helices.

Figure 14:
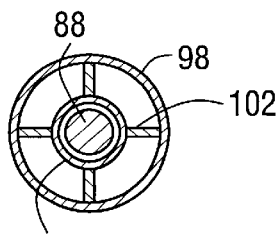
FIG. 14 is a cross-section along the line XIV—XIV of FIG. 11.
Figure 12:
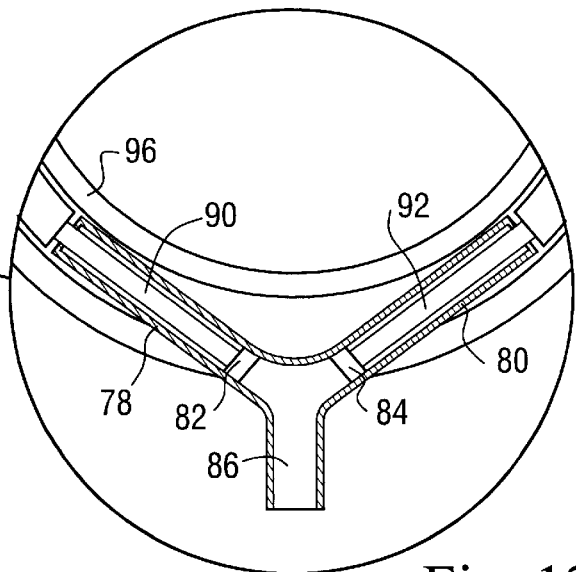

FIGS. 11–14 show an embodiment of the device of the invention in which a hydraulic motor comprises two interconnected cylinders 78 and 80 and two pistons 82 and 84 in the respective cylinders 78,80. The cylinders 78,80 have a common fluid supply inlet member 86, which together with the cylinders 78,80 takes the shape of a Y-pipe. The restriction member comprises an elongated resilient arcuate core 88. The adjustment device comprises two bars 90 and 92 secured to opposite ends of the core 88 and connected to the pistons 82 and 84, respectively. The core 88 defines a restriction opening and is provided with a releasable and lockable joint 94 (FIG. 13) to permit application of the core 88 around the esophagus or stomach. The core 88 and the cylinders 90,92 are enclosed by a soft elastic hose 96 except at the joint 94 and the inlet member 86. The hose 96 has an outer tubular wall 98 and a central coaxial inner tubular wall 100, which is fixed to the outer wall 98 by spoke members 102 (FIG. 14). The core 88 is loosely fit in the inner tubular wall 100. By supplying fluid to or withdrawing fluid from the inlet 86 the pistons 82 and 84 will move towards or from each other, so that the restriction opening defined by the core 88 is changed by the longitudinal displacement of the bars 90,92.

Figure 15:
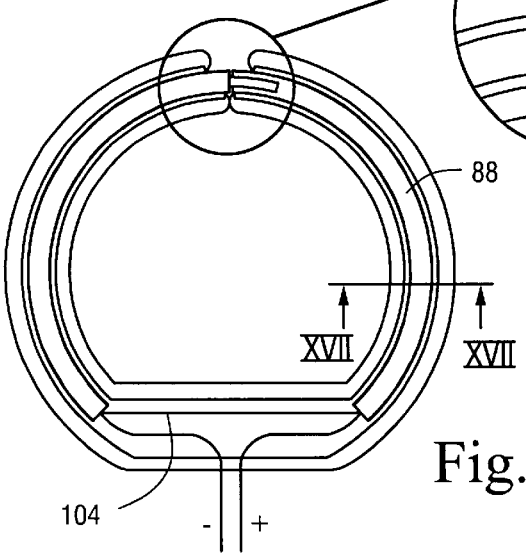
FIG. 15 is a schematic view of a fifth embodiment of the apparatus in accordance with the invention.
Figure 16:
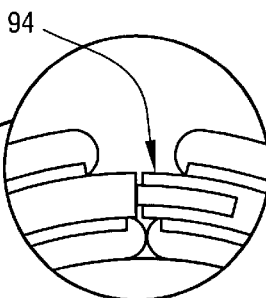
FIG. 16 is an enlarged detail of FIG. 15.
Figure 17:
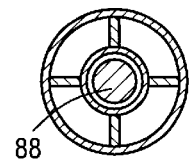
FIG. 17 is a cross-section along the line XVII—XVII of FIG. 15.

FIGS. 15–17 show an embodiment of the invention which is identical to the embodiment of FIGS. 11–14, except that the adjustment device comprises an elongated voltage responsive element 104 secured to the opposite ends of the core 88, so that the core 88 and the element 104 form the restriction member. The element 104 is capable of bending inwardly into a bow in response to a voltage applied across the element 104. The radius of curvature of said bow is adjustable by changing the level of the voltage applied to element 104.

FIG. 18 shows an embodiment of the invention comprising a loop forming means in the form of a substantially rigid outer circular element 106 with a releasable and lockable joint 108. In this embodiment the restriction member comprises an elastic inner circular element 110 formed by the innermost wall portion of an elastic hose 112 extending along the outer element 106. The inner circular element 110 is disposed concentrically within the outer circular element 106. The adjustment device comprises a plurality of threads 114 secured to the elastic inner element 110 along the circumference thereof and running from the inner element 110 via guide members 116 attached to the outer element 106. By pulling all the threads 114 the inner elastic element 110 is pulled under expansion radially outwardly towards the outer element 106.

FIG. 19 shows an embodiment which is identical to the embodiment of FIG, 9, except that it comprises a loop forming means in the form of a substantially rigid outer circular element 118 supporting the helical springs 60,62, and a soft elastic inner wall 120 extending along the springs 60,62. When the motor 68 rotates the helical springs 60,62 in a direction that enlarges the coils of the springs 60,62, the coils are forced by the rigid outer element 118 to expand radially inwardly thereby reducing the size of the restriction opening formed by the circumferential confinement surface of the restriction member (springs 60,62 and body 64).

FIG. 20 shows an embodiment of the invention in which a restriction member comprises a plurality of arcuate lamellae 122 arranged like the conventional adjustable aperture mechanism of a camera. The adjustment device, not shown, is conventional and is operated by a motor 124 to adjust the lamellae 122 to change the size of an restriction opening defined by the lamellae 122.

FIGS. 21–23 show an embodiment of the invention in which a restriction member comprises two semi-circular elements 126 and 128 which are hinged together such that the semi-circular elements 126,128 are swingable relative to each other between a fully open state in which they substantially form a circle, illustrated in FIG, 22 and an angular state, in which the size of the restriction opening defined by the semi-circular elements 126,128 is reduced, illustrated in FIG, 23. The adjustment device, not shown, is conventional and is operated by a motor 130 to swing the semi-circular elements 126,128 relative to each other.

FIGS. 24–27 show an embodiment of the invention in which a restriction member comprises an elastic belt 130 forming a circle and having a substantially oval cross-section. The restriction member 130 is provided with a releasable and lockable joint 132. An elastic double walled hose 134 encloses the belt 130 except at the joint 132. The adjustment device, not shown, is conventional and is operated by a motor 136 to turn the belt 130 around the longitudinal extension thereof between a fully open state, in which the inner broader side of the belt 130 forms a substantially cylindrical surface, illustrated in FIG. 26, and a reduced open state, in which the inner broader side of the belt 130 forms a substantially conical surface, illustrated in FIG. 27.

FIG. 28 schematically illustrates a cushion arrangement for protecting the esophagus or stomach, comprising a plurality of cushions 138 disposed in series along a substantially circular holding member 140. This cushion arrangement may be utilized in any of the above described embodiments of the invention.

Figure 29A:
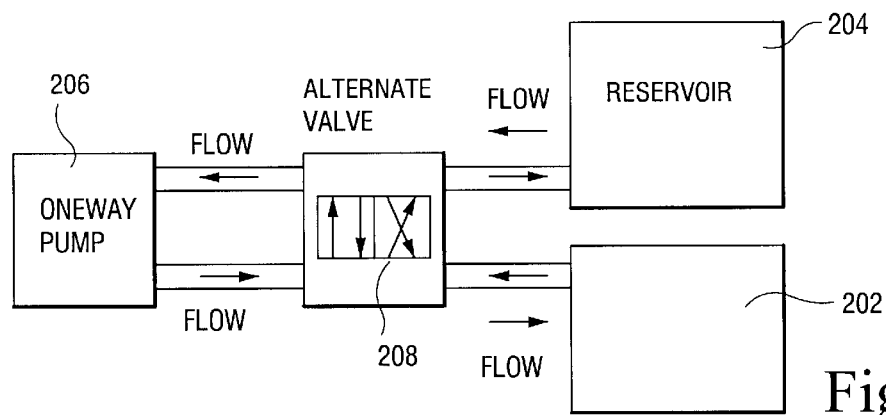
FIG. 29A–D is a block diagram of four different principal embodiments of the invention.
Figure 29B:
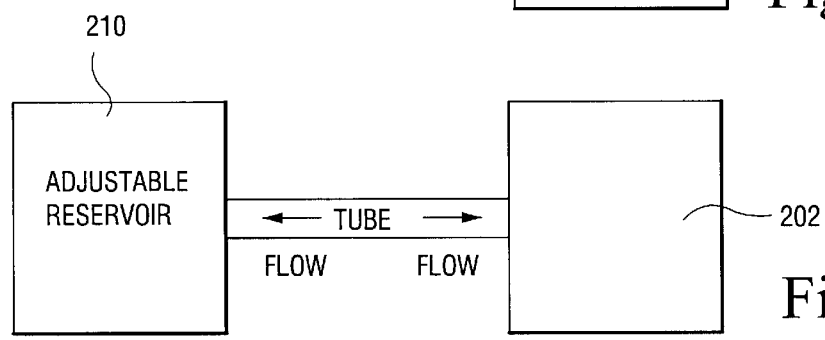
Figure 29C:
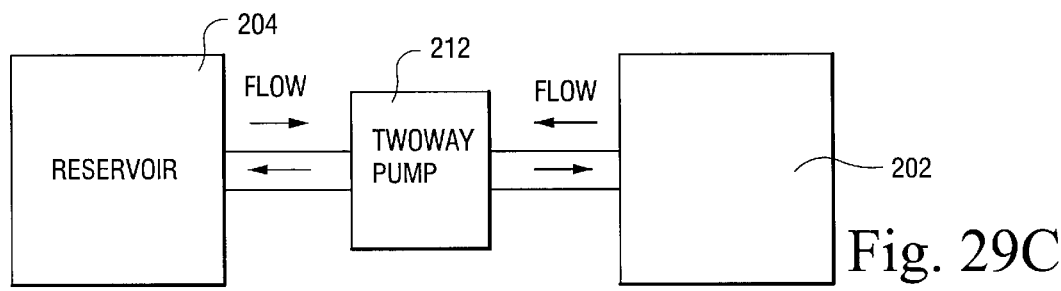

FIGS. 29A–D provide a block diagram of four different hydraulic transmission configurations. FIG. 29A shows an adjustment device 202, a separate reservoir 204, a one way pump 206 and an alternate valve 208. FIG. 29B shows the adjustment device 202 and an adjustable reservoir 210. FIG. 29C shows the adjustment device 202, a two way pump 212 and the reservoir 204. FIG. 30D shows a servo system with a first closed system controlling a second system. The servo system comprises the adjustable reservoir 210 and a passive adjustable reservoir 214. Any of the reservoirs can be the active reservoir, either the servo reservoir 210 or the fluid supply reservoir 214. The reservoir 214 controls a larger adjustable reservoir 216 which is used for the operation of the adjustment means 202 for changing the restriction opening of the restriction member.

Figure 30A:
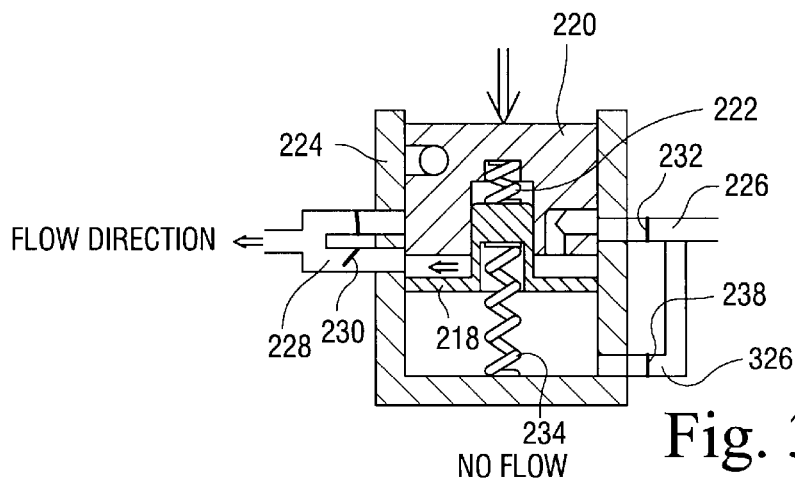
FIG. 30A–D are cross-sectional views of a pump mechanism according to FIG. 29C, which pumps fluid in opposite directions by mechanically pushing a wall portion in only one direction.
Figure 30B:
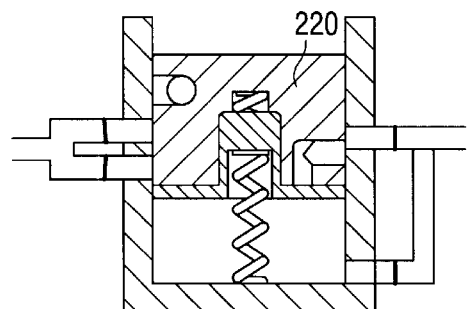
Figure 30C:
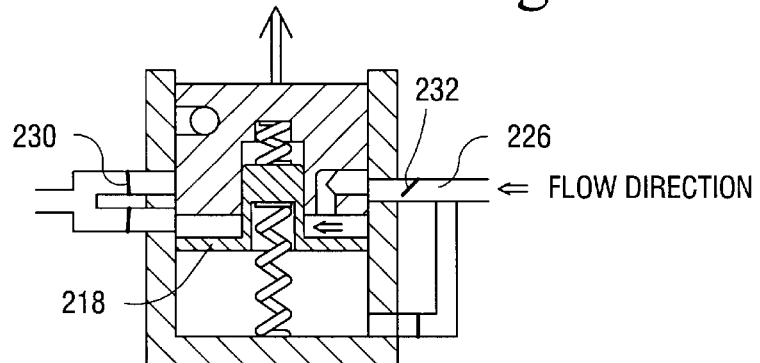

FIGS. 30A–D are cross-sectional views of a pump mechanism adapted to pump fluid in both directions only by mechanically pushing a separate sealing wall portion 218 in one direction. FIG. 30A shows a piston 220 pushed forwards against a spring 222 towards the wall portion 218 and located in a pump housing 224 conducting fluid from a right upper fluid passage 226 of the housing 224 to a left fluid passage 228 of the housing 224. A main valve 230 is open and a nonreturn valve 232 is closed. FIG. 30B illustrates the first pump movement in which the piston 220 has moved forwards and reaches the wall portion 218. FIG. 30C illustrates how the piston 220 moves backwards by the action of the spring 222. The main valve 230 is now closed and the nonreturn valve 232 is open for fluid from the right upper passage 226. FIG. 30D illustrates how the piston 220 is moved further downwards from its position according to FIG. 30B while pushing the wall portion 218 downwards against a second spring 234 that is stronger than spring 222, so that fluid escapes from a right lower fluid passage 236. When moving the piston 220 backwards from the position of FIG. 30D, fluid enters the left fluid passage 228 and a valve 238 in the lower right fluid passage 236 closes.

Figure 29D:
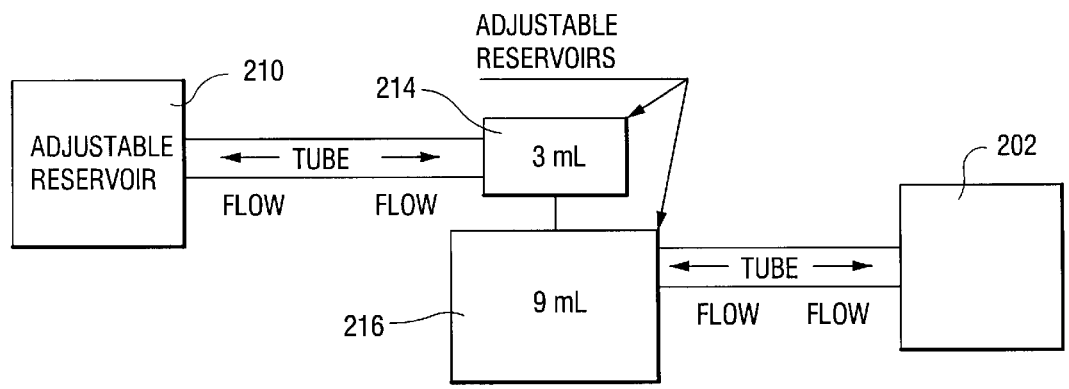
Figure 30D:
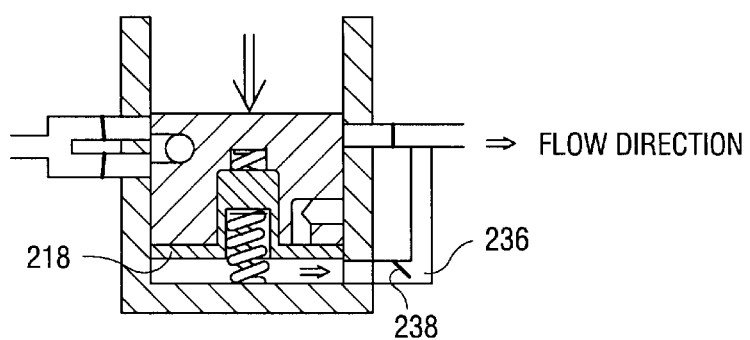
Figure 31:
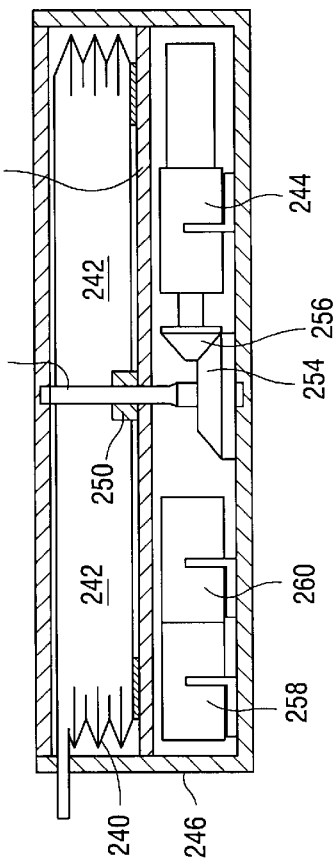
FIG. 31 is a cross-sectional view of a reservoir having a variable volume controlled by a remote control motor, in accordance with a particular embodiment of the principal embodiment shown in FIG. 29B or 30B.

FIG. 31 is a cross-sectional view of a reservoir 240 defining a chamber 242, the size of which is variable and is controlled by a remote controlled motor 244, in accordance with FIG. 29B or 29D. The reservoir 240 and the motor 244 are placed in a housing 246. The chamber 242 is varied by moving a large wall 248. The wall 248 is secured to a nut 250, which is threaded on a rotatable spindle 252. The spindle 252 is rotated by the motor 244 via an angular gearing, which comprises two conical gear wheels 254 and 256 in mesh with each other. The motor 244 is powered by a battery 258 placed in the housing 246. A signal receiver 260 for controlling the motor 244 is also placed in the housing 246. Alternatively, the battery 258 and the signal receiver 260 may be mounted in a separate place. The signal receiver may comprise any known or conventional device which is capable of receiving a control signal and then operating the motor 244.

Figure 32:
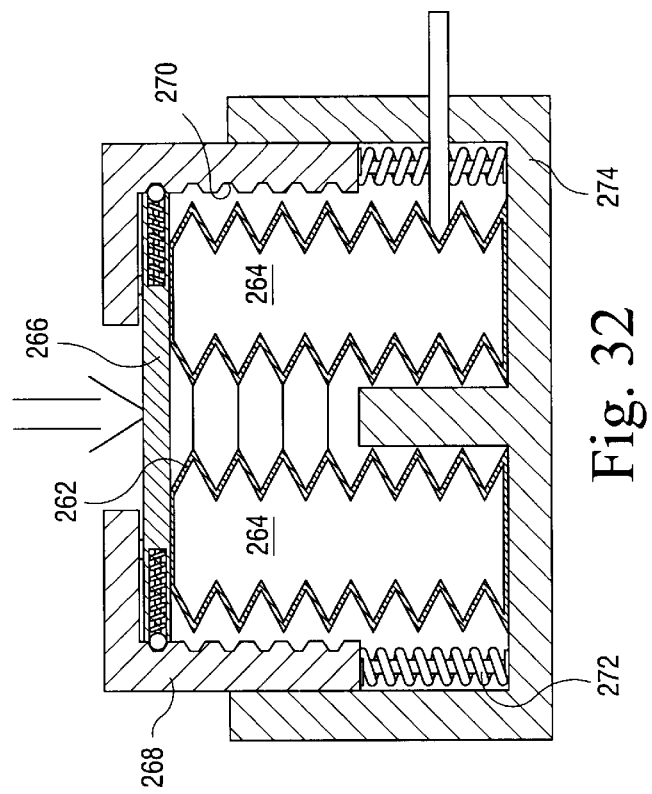
FIG. 32 is a cross-sectional view of a reservoir having a variable volume adjustable by manual manipulation, in accordance with a particular embodiment of the principal embodiment shown in FIG. 29B or 29D.

FIG. 32 is a cross-sectional view of a reservoir 262 defining a chamber 264, the size of which is variable and is controlled by manual manipulation. A gable wall portion 266 of an open ended inner cylindrical housing 68 is adapted to be pushed downwards to fit in a desired locking groove 270 of a plurality of locking grooves 270 on the mantle wall of the cylindrical housing 268, to reduce the size of the chamber 64. The inner cylindrical housing 268 is suspended by springs 272 and is telescopically applied on an outer cylindrical housing 274. When pushing the inner cylindrical housing 268 it moves downwards relative to the outer cylindrical housing 274 causing the gable wall portion 266 to release from the locking groove 270 and move upwards relative to the inner cylindrical housing 268. When the inner housing 268 is moved upwardly by the action of the springs 272 the size of the chamber 264 is increased.

FIG. 33A and 33B show a servo means comprising a main ring-shaped fluid reservoir 276 defining a chamber 278, the size of which is variable. Centrally positioned in the main ring-shaped reservoir 276 there is a servo fluid reservoir 280 defining a chamber 282, the size of which is variable. The chamber 282 of the servo reservoir 280 is significantly smaller than the chamber 278 of the main reservoir 276. The two reservoirs 276 and 280 are situated between two opposite separate walls 284 and 286, and are secured thereto. When changing the amount of fluid in the servo reservoir 280, the two opposite walls 284,286 are moved towards or away from each other, whereby the size of the chamber 278 of the main reservoir 276 is changed.

Figure 34:
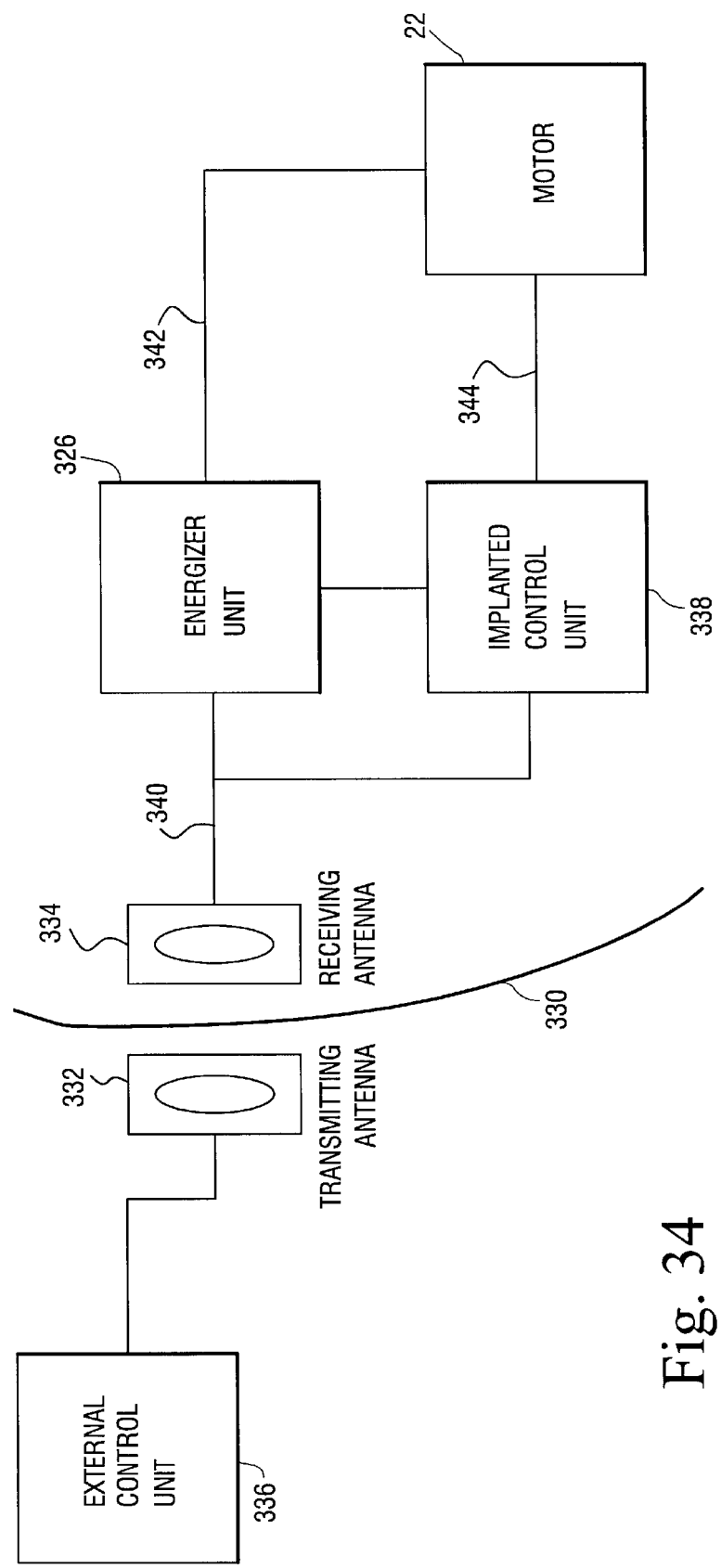
FIG. 34 is a block diagram illustrating remote control components of the apparatus of the invention.

FIG. 34 shows the basic parts of a remote control system of the apparatus of the invention including a motor, for instance the electric motor 22. In this case, the remote control system is based on the transmission of electromagnetic wave signals, often of high frequencies in the order of 100 kHz–1 gHz, through the skin 330 of the patient. In FIG. 34, all parts placed to the left of the skin 330 are located outside the patient's body and all parts placed to the right of the skin 330 are implanted in the patient's body.

An external signal transmitting antenna 332 is to be positioned close to a signal receiving antenna 334 implanted in the patient's body close to the skin 330. As an alternative, the receiving antenna 334 may be placed for example inside the abdomen of the patient. The receiving antenna 334 comprises a coil, approximately 1–100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 332 comprises a coil having about the same size as the coil of the receiving antenna 334 but wound with a thick wire that can handle the larger currents that is necessary. The coil of the transmitting antenna 332 is tuned to the same specific high frequency as the coil of the receiving antenna 334.

An external control unit 336 comprises a microprocessor, a high frequency electromagnetic signal generator and a power amplifier. The microprocessor of the control unit 336 is adapted to switch on/off the generator and to modulate signals generated by the generator to send digital information via the power amplifier and the antennas 332,334 to an implanted control unit 338. To avoid that accidental random high frequency fields trigger control commands, digital signal codes are used. A keypad placed on the external control unit 336 is connected to the microprocessor thereof. The keypad is used to order the microprocessor to send digital signals to either increase or decrease the size of the restriction opening defined by the loop of the restriction member (e.g. as described above). The microprocessor starts a command by applying a high frequency signal on the antenna 332. After a short time, when the signal has energized the implanted parts of the control system, commands are sent to increase or decrease the size of the restriction opening of the restriction member in predefined steps. The commands are sent as digital packets in the form illustrated below.

| Start pattern, 8 bits | Command, 8 bits | Count, 8 bits | Checksum, 8 bits |
| --- | --- | --- | --- |

The commands are sent continuously during a rather long time period (e.g. 30 seconds or more). When a new increase or decrease step is desired the Count byte is increased by one to allow the implanted control unit 338 to decode and understand that another step is demanded by the external control unit 336. If any part of the digital packet is erroneous, its content is simply ignored.

Through a line 340, an implanted energizer unit 326 draws energy from the high frequency electromagnetic wave signals received by the receiving antenna 334. The energizer unit 326 stores the energy in a power supply, such as a large capacitor, powers the control unit 338 and powers the electric motor 22 via a line 342.

The control unit 338 comprises a demodulator and a microprocessor. The demodulator demodulates digital signals sent from the external control unit 336. The microprocessor of the control unit 338 receives the digital packet, decodes it and, provided that the power supply of the energizer unit 326 has sufficient energy stored, sends a signal via a signal line 344 to the motor 22 to either increase or decrease the size of the restriction opening of the restriction member depending on the received command code.

Alternatively, the energy stored in the power supply of the energizer unit may only be used for powering a switch, and the energy for powering the motor 22 may be obtained from another implanted power source of relatively high capacity, for example a battery. In this case the switch is adapted to connect the battery to the control unit 338 in an "on" mode when said switch is powered by said power supply and to keep said battery disconnected from the control unit in a "standby" mode when the switch is unpowered.

Figure 35:
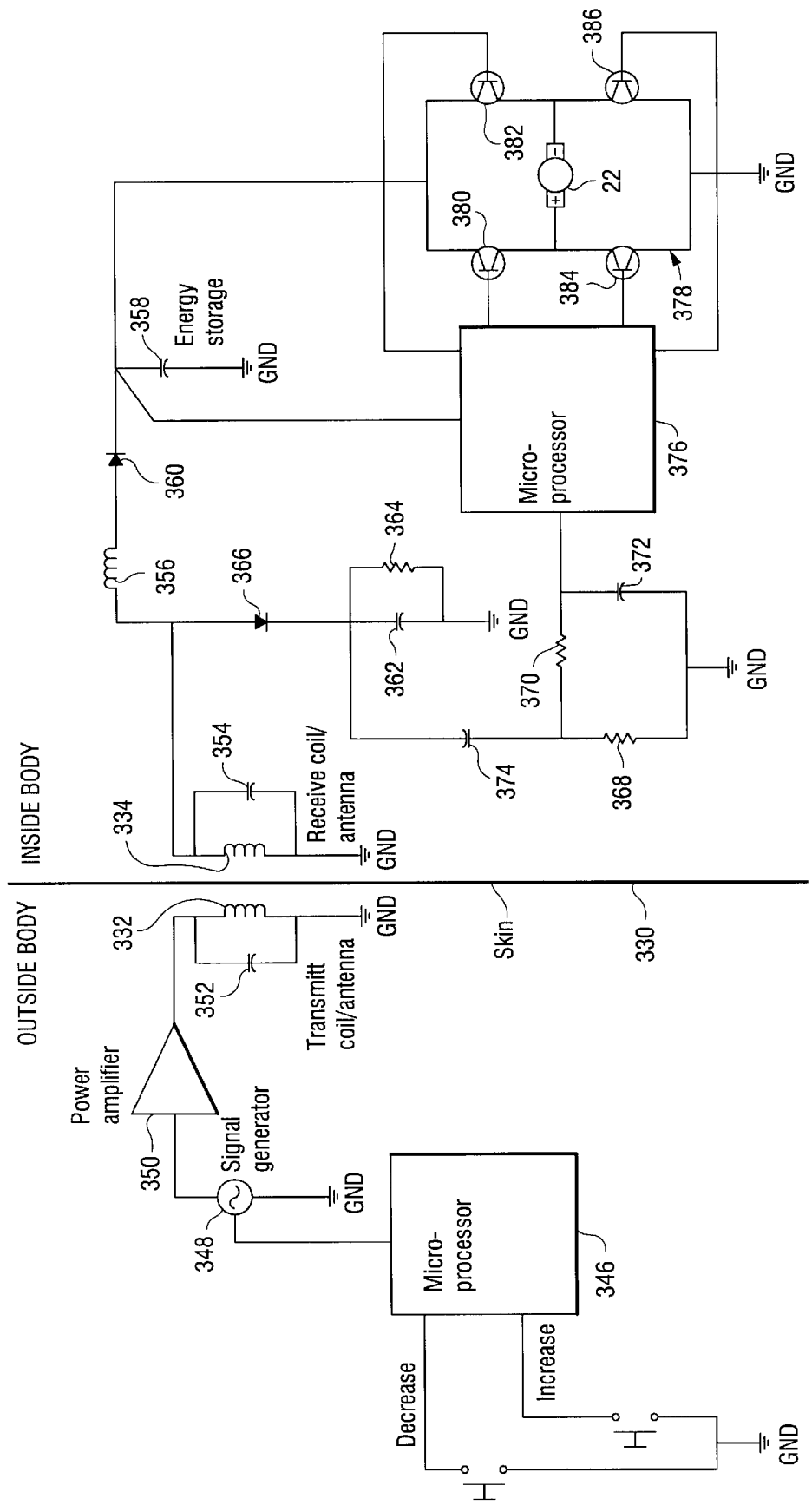
FIG. 35 is a schematic view of a circuitry used for the system of the block diagram of FIG. 34.

With reference to FIG. 35, the remote control system schematically described above will now be described in accordance with a more detailed embodiment. The external control unit 336 comprises a microprocessor 346, a signal generator 348 and a power amplifier 350 connected thereto. The microprocessor 346 is adapted to switch the signal generator 348 on/off and to modulate signals generated by the signal generator 348 with digital commands that are sent to implanted components of the device of the invention. The power amplifier 350 amplifies the signals and sends them to the external signal transmitting antenna 332. The antenna 332 is connected in parallel with a capacitor 352 to form a resonant circuit tuned to the frequency generated by the signal generator 348.

The implanted signal receiving antenna coil 334 forms together with a capacitor 354 a resonant circuit that is tuned to the same frequency as the transmitting antenna 332. The signal receiving antenna coil 334 induces a current from the received high frequency electromagnetic waves and a rectifying diode 360 rectifies the induced current, which charges a storage capacitor 358. A coil 356 connected between the antenna coil 334 and the diode 360 prevents the capacitor 358 and the diode 360 from loading the circuit of the signal receiving antenna 334 at higher frequencies. Thus, the coil 356 makes it possible to charge the capacitor 358 and to transmit digital information using amplitude modulation.

A capacitor 362 and a resistor 364 connected in parallel and a diode 366 forms a detector used to detect amplitude modulated digital information. A filter circuit is formed by a resistor 368 connected in series with a resistor 370 connected in series with a capacitor 372 connected in series with the resistor 368 via ground, and a capacitor 374, one terminal of which is connected between the resistors 368, 370 and the other terminal of which is connected between the diode 366 and the circuit formed by the capacitor 362 and resistor 364. The filter circuit is used to filter out undesired low and high frequencies. The detected and filtered signals are fed to an implanted microprocessor 376 that decodes the digital information and controls the motor 22 via an H-bridge 378 comprising transistors 380,382,384 and 386. The motor 22 can be driven in two opposite directions by the H-bridge 378.

The microprocessor 376 also monitors the amount of stored energy in the storage capacitor 358. Before sending signals to activate the motor 22, the microprocessor 376 checks whether the energy stored in the storage capacitor 358 is enough. If the stored energy is not enough to perform the requested operation, the microprocessor 376 waits for the received signals to charge the storage capacitor 358 before activating the motor 22.

FIGS. 36A and 36B show an embodiment of the apparatus of the invention comprising a restriction device 402 having an elongated flexible restriction member 404, such as a belt, a cord or the like. The flexible member 404 extends in a loop around the esophagus 406 (or stomach). (Alternatively, the flexible member 404 may comprise two separate parts on opposite sides of the esophagus.) One portion 404A of member 404 is attached to a frame 408 and another portion 404B of member 404 opposite portion 404A in the loop of the flexible member 404 is connected to an adjustment device 410, which is fixed to the frame 408. The adjustment device 410 pulls the flexible member 404 in the direction from portion 404A to squeeze esophagus between two opposite lengths of the flexible member 404 to thereby decrease the cross-sectional area in the esophagus (or stomach), see FIG. 36A, and releases the esophagus from the flexible member 404 to thereby increase the cross-sectional area in the esophagus 406, see FIG. 36B.

FIGS. 37A and 37B show an embodiment of the apparatus of the invention comprising a restriction device 412 having two rigid plate or bar elements 414 on opposite sides of the esophagus 406 (or stomach). An adjustment device 416 moves the rigid elements 412 in parallel towards each other to squeeze the esophagus 406 between the rigid elements 412 to thereby decrease the cross-sectional area in the esophagus, see FIG. 37A, and moves the rigid elements 412 away from each other to increase the cross-sectional area in the esophagus 406, see FIG. 37B.

FIG. 38 shows an embodiment of the apparatus of the invention comprising a restriction device 418 having two rigid articulated clamping elements 420 positioned on opposite sides of the esophagus 406 (or stomach) like the blades of a scissor. An adjustment device 422 turns the clamping elements 420 toward each other to clamp the esophagus 406 between the clamping elements 420 to thereby decrease the cross-sectional area in the esophagus 406, and turns the clamping elements 420 away from each other to release the esophagus 406 from the clamping elements 420 to thereby increase the cross-sectional area in the esophagus 406.

FIGS. 39A, 39B and 39C show an embodiment of the apparatus of the invention comprising a restriction device 424 having three bending members in the form of cylindrical rollers 426,428 and 430 displaced relative one another in a row along the esophagus 406 (or stomach) and positioned alternately on opposite sides of the esophagus 406. (Alternatively, each roller 426,428 and 430 may take the shape of an hour-glass.) An adjustment device 432 moves the two outer rollers 426,430 laterally against the esophagus 406 in one direction and the intermediate roller 428 against the esophagus 406 in the opposite direction to bend the esophagus to thereby decrease the cross-sectional area in the esophagus 406, see FIG. 39B. To increase the cross-sectional area in the esophagus 406 the adjustment device 432 moves the rollers 426–430 away from the esophagus 406 to release the latter from the rollers 426–430, see FIG. 39C.

Figure 40A:
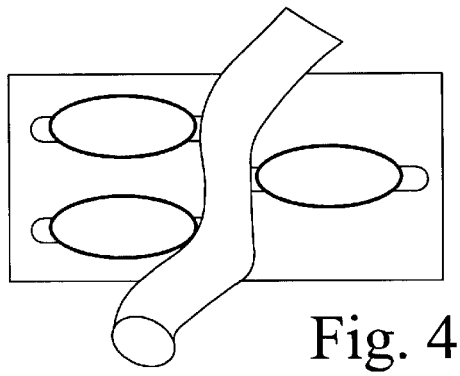
Figure 40B:
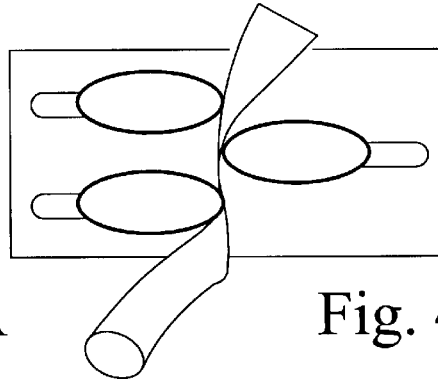
Figure 41A:
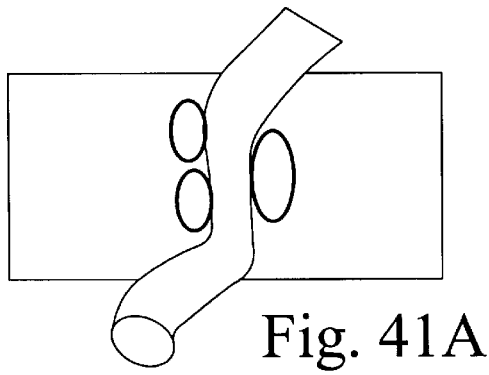
Figure 41B:
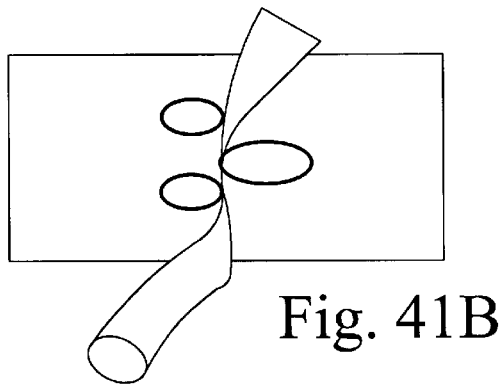
Figure 42A:
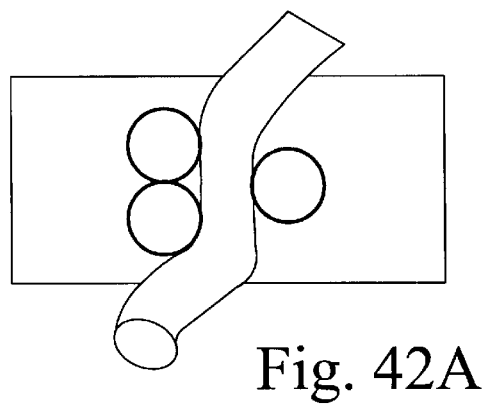
Figure 42B:
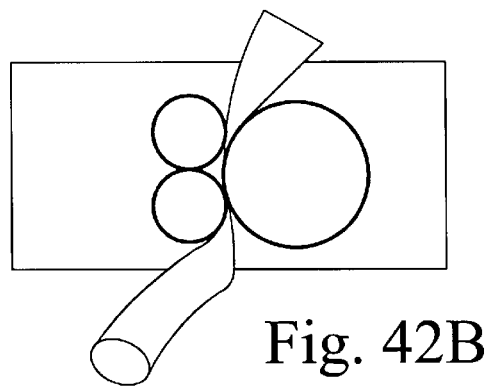

FIGS. 40A through 44B schematically illustrates modifications of the above embodiment according to FIGS. 39A–39C. Thus, FIGS. 40A and 40B show an embodiment similar to that of FIGS. 39A–39C except that the bending members are oval and not rotatable. FIGS. 41A and 41B show an embodiment similar to that of FIGS. 40A and 40B except that the oval bending members are rotatable to release the esophagus (or stomach), see FIG. 41A, and squeeze the esophagus, see FIG. 41 B. FIGS. 42A and 42B show an embodiment similar to that of FIGS. 39A–39C except that the intermediate roller has a changeable diameter to release the esophagus (or stomach), see FIG. 42A, and squeeze the esophagus, see FIG. 42B. FIGS. 43A and 43B show an embodiment similar to that of FIGS. 37A–37C except that the rigid elements are replaced by two cylindrical rollers positioned on opposite sides of the esophagus. Finally, FIGS. 44A and 44B show an embodiment substantially similar to that of FIGS. 43A and 43B except that the restriction device is turned 90? to form a S-shaped curvature of the esophagus.

Figure 45:
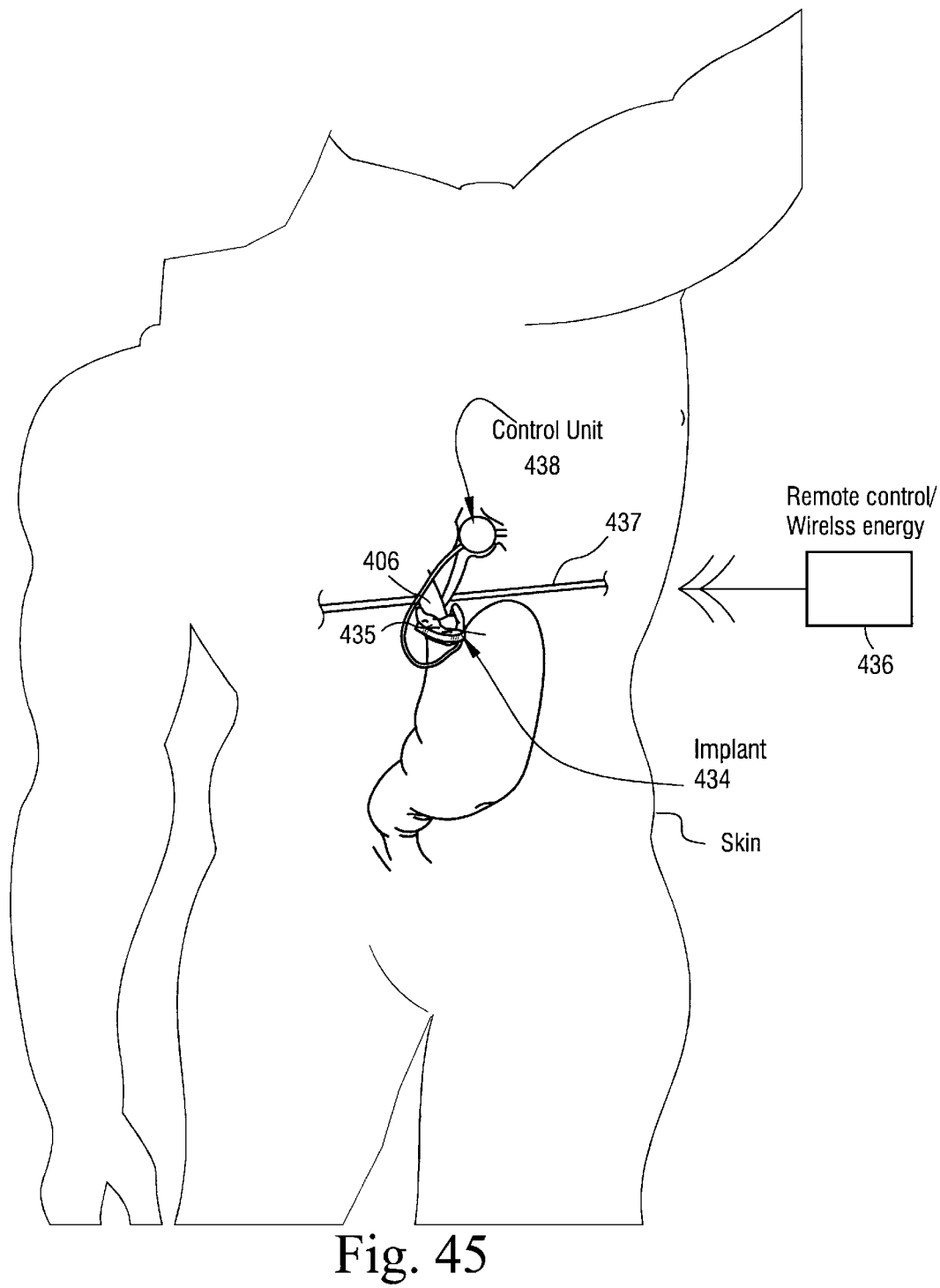
FIG. 45 illustrates the apparatus in accordance with the invention implanted in a patient.

FIG. 45 illustrates how any of the above-described embodiments of the heartburn and reflux disease treatment apparatus of the invention may be implanted in a patient. Thus, an assembly 434 of the apparatus implanted in the patient comprises an adjustable restriction device engaging the esophagus 406 close to the cardia and an adjustment device for adjusting the restriction device. The restriction device of the assembly 434 is provided with a soft support member 435, which abuts upwardly against the diaphragm 437 of the patient. A wireless remote control of the apparatus comprises an external signal transmitter 436 and an implanted signal receiver 438, which comprises a control unit for controlling the adjustment device of the implanted assembly 434 in response to signals from the transmitter 436. The signal receiver 438 further comprises an energizer unit which transfers energy from the signals transmitted by the transmitter 436 into electric energy for energy consuming implanted components of the apparatus.

There are a number of other conceivable alternative embodiments of the invention that give the same result as the above-described embodiments. For example, the microprocessor of the external and implanted, respectively, control unit may be replaced by discrete components. The power amplifier of the external control unit may be omitted if the signals generated by the signal generator are strong enough. Therefore the invention is to be accorded the broadest interpretation of the appended claims to encompass all equivalent structures and assemblies.

One further advantage with this invention is that there may be a night button on the remote control setting the adjustment device in a position with a larger cross-sectional area of the food passage in the esophagus or stomach during the night, thus avoiding vomiting or nausa. Both the amount of restriction and time schedule are preferable programmed from outside the patient's body. A sensor sensing for example the position of the patient may be used in a feedback regulation system.

In the practice of the present invention the details of the elongated restriction device (such as a gastric band) and the adjustment/operation device (which may have electric, hydraulic, or mechanical, etc. actuation), may be as described in copending applications Ser. No. 09/133,319, filed Aug. 13, 1998 (Atty Ref: 2333-12), Ser. No. 09/133, 320, filed Aug. 13, 1998 (Atty Ref: 2333-11) and Ser. No. 09/133,322, filed Aug. 13, 1998 (Atty Ref: 2333-13), the disclosures of which are incorporated by reference herein.

What is claimed is:

1. A heartburn and reflux disease treatment comprising:
   an adjustable non-inflatable restriction device adapted to be implanted in a patient having heartburn and reflux disease to engage the esophagus or the stomach close to the cardia without forming an upper pouch of the stomach that substantially accumulates food to form a restricted cross-sectional area of the food passageway in the stomach or esophagus, said restriction device being designed to work like an artificial sphincter to allow food to readily pass through the passageway, and
   a post-operation adjustment device for mechanically non-invasively adjusting said restriction device to change the size of the cross-sectional area sufficiently so as to substantially prevent regurgitation of stomach acids or foods into the patient's esophagus.

2. The apparatus according to claim 1, wherein said restriction device comprises an elongated restriction member and forming means adapted to form said restriction member into at least a substantially closed loop around the esophagus or stomach, said loop defining a restriction opening, whereby said adjustment device adjusts said restriction member in said loop to change the size of said restriction opening.

3. The apparatus according to claim 2, wherein said adjustment device adjusts the longitudinal extension of said elongated restriction member.

4. The apparatus according to claim 3, wherein said restriction member comprises a main portion and two elongated end portions, and said adjustment device establishes a longitudinal relative displacement between said end portions of said restriction member, such that the size of said restriction opening is adjusted.

5. The apparatus according to claim 4, wherein said adjustment device comprises a movement transferring member in engagement with at least one of said end portions of said restriction member and operable to displace said one end portion relative to said other end portion of said restriction member.

6. The apparatus according to claim 5, further comprising a motor, which is fixed relative to said main portion of said restriction member and has a rotating drive shaft operatively connected to said movement transferring member.

7. The apparatus according to claim 6, wherein said motor is positioned relative to said elongated restriction member such that said drive shaft extends in parallel with a chord in said loop of the restriction member.

8. The apparatus according to claim 3, wherein said elongated restriction member is longitudinally resilient and said adjustment device comprises a contraction device, which longitudinally contracts said resilient restriction member.

9. The apparatus according to claim 8, wherein said elongated restriction member comprises a substantially non-resilient main portion and an end portion forming an elongated helical spring, which is contractable by said contraction device.

10. The apparatus according to claim 9, wherein said contraction device comprises an elongated flexible pulling member connected to said main portion of said restriction member and extending through said helical spring to contract said helical spring against an arresting member, which is fixed relative to said main portion of said restriction member.

11. The apparatus according to claim 3, wherein said restriction member comprises an elongated helical spring having a free end, and a body to which said spring is nonrotatably secured at its opposite end, said adjustment means device rotates said helical spring in one direction to enlarge the coils of said helical spring to longitudinally contract said elongated helical spring and to rotate said helical spring in the opposite direction to reduce the size of the coils of said helical spring to longitudinally extend said helical spring.

12. The apparatus according to claim 11, wherein said restriction member comprises a further elongated helical spring having a free end and nonrotatably secured to said body at its opposite end, and said adjustment device comprises a drive shaft having two opposite end portions connected to said helical springs, respectively, at their free ends, said helical coils forming left and right hand helices, respectively.

13. The apparatus according to claim 12, wherein said restriction member comprises a further elongated helical spring having a free end and nonrotatably secured to said body at its opposite end, and said adjustment device comprises a gearing having an input shaft and two opposite aligned output shafts connected to said helical springs, respectively, at their free ends, said input shaft being connected to said output shafts such that said output shafts rotate in opposite directions upon rotation of said input shaft, said helical coils forming the same helices.

14. The apparatus according to claim 3, further comprising a motor operatively connected to said adjustment device.

15. The apparatus according to claim 14, wherein said motor is fixed to said restriction member.

16. The apparatus according to claim 15, wherein said motor is remote from said restriction member and is connected to said adjustment device by a power transmission conduit.

17. The apparatus according to claim 2, wherein said restriction member forms a radially innermost at least partly circumferential confinement surface of said restriction member, and said adjustment device mechanically adjusts said restriction member such that at least a portion of said confinement surface is substantially radially displaced in said loop.

18. The apparatus according to claim 17, wherein said adjustment device comprises an elongated voltage responsive element forming part of said confinement surface and capable of bending into a bow in response to a voltage applied across said element, the radius of curvature of said bow being adjustable by changing the level of said voltage.

19. The apparatus according to claim 17, wherein said restriction member comprises an elastic annular element forming said confinement surface, and said adjustment device changes the diameter of said elastic annular element.

20. The apparatus according to claim 17, wherein said forming means comprises a substantially rigid outer annular element, and said restriction member comprises an elongated helical spring extending internally along said outer annular element and contacting the latter, said helical spring forming part of said circumferential confinement surface and having a free end, and a body to which said helical spring is nonrotatably secured at its opposite end, said adjustment device rotates said helical spring in one direction to enlarge the coils of said helical spring to contract said circumferential confinement surface and to rotate said helical spring in the opposite direction to reduce the size of the coils of said helical spring to expand said circumferential confinement surface.

21. The apparatus according to claim 17, wherein said forming means comprises a substantially rigid outer annular element, and said restriction member comprises a first and a second elongated helical spring extending internally along said outer annular element and contacting the latter, said helical springs forming part of said circumferential confinement surface, said first and said second spring, respectively, having a free end, and a body to which said first and said second spring, respectively, is nonrotatably secured at its opposite end, said adjustment device rotating said first and said second spring, respectively, in one direction to enlarge the coils of said spring to contract said circumferential confinement surface and to rotate said first and said second spring, respectively, in the opposite direction to reduce the size of the coils of said spring to expand said circumferential confinement surface.

22. The apparatus according to claim 17, further comprising a motor operatively connected to said adjustment device.

23. The apparatus according to claim 22, comprising a reversing device adapted to be implanted in the patient for reversing said motor.

24. The apparatus according to claim 2, wherein said forming means form said restriction member into a loop having a predetermined size.

25. The apparatus according to claim 2, wherein said elongated restriction member is flexible, and said adjustment device pulls a first portion of said flexible restriction member from a second portion of said flexible restriction member opposite said first portion in said loop to squeeze the esophagus or stomach between two opposite lengths of said elongated flexible restriction member to decrease the cross-sectional area in the esophagus or stomach and moves said first portion toward said second portion of said restriction member to release the esophagus or stomach from said flexible restriction member to increase the cross-sectional area.

26. The apparatus according to claim 2, wherein said restriction member comprises at least two separate elements, at least one of which is pivoted such that it may turn in a plane in which said loop of said restriction member extends, and said adjustment device turns said pivoted element to change the size of said restriction opening.

27. The apparatus according to claim 2, wherein said restriction member comprises at least two frame elements, which are foldable towards each other by said adjustment device.

28. The apparatus according to claim 27, wherein said foldable frame elements comprise two substantially or partly semi-circular frame elements, which are hinged together such that said semi-circular elements are swingable relative to each other from a fully open state in which they substantially or partly form a circle to a fully folded state in which they substantially form a semi-circle.

29. The apparatus according to claim 2, wherein said elongated restriction member is elastic and varies in thickness as seen in a cross-section therethrough, and said adjustment device turns said restriction member around the longitudinal extension thereof.

30. The apparatus according to claim 2, further comprising a hydraulic device which operates said adjustment device.

31. The apparatus according to claim 30, further comprising a reservoir containing a predetermined amount of fluid for supplying said hydraulic device with fluid.

32. The apparatus according to claim 31, wherein said reservoir defines a chamber for said predetermined amount of fluid and said hydraulic device changes the volume of said chamber.

33. The apparatus according to claim 31, wherein said hydraulic device comprises an activatable pump for pumping fluid between said reservoir and said adjustment device.

34. The apparatus according to claim 31, wherein said hydraulic device comprises a servo means.

35. The apparatus according to claim 34, wherein said hydraulic device comprises first and second wall portions of said reservoir, and said servo means provides relative displacement between said first and second wall portions of said reservoir.

36. The apparatus according to claim 2, wherein said adjustment device changes the size of said restriction opening such that the outer circumferential confinement surface of said restriction member is changed.

37. The apparatus according to claim 2, wherein said adjustment device changes the size of said restriction opening such that the outer circumferential confinement surface of the restriction member is unchanged.

38. The apparatus according to claim 2, wherein said forming means comprises a spring material forming said elongated restriction member into said loop, such that said restriction opening has a predetermined size, and said adjustment device adjusts said restriction member against the spring action of said spring material.

39. The apparatus according to claim 38, wherein said spring material is integrated in said restriction member.

40. The apparatus according to claim 1, further comprising a wireless remote control for non-invasively controlling said adjustment device.

41. The apparatus according to claim 40, wherein said remote control comprises a separate signal transmitter and/or receiver and a signal receiver and/or transmitter adapted to be implanted in the patient.

42. The apparatus according to claim 41, wherein said signal transmitter and signal receiver transmit and receive signals in the form of digital pulses.

43. The apparatus according to claim 42, wherein said digital pulses comprise an electric or magnetic field.

44. The apparatus according to claim 41, wherein said signal receiver comprises a control unit for controlling said adjustment device in response to signals received from said signal transmitter.

45. The apparatus according to claim 44, further comprising an energizer unit adapted to be implanted in the patient for providing energy to energy consuming components of said restriction device.

46. The apparatus according to claim 45, further comprising a motor adapted to be implanted in the patient for operating said adjustment device.

47. The apparatus according to claim 46, wherein said control unit powers said motor with energy provided by said energizer unit in response to signals received from said signal transmitter.

48. The apparatus according to claim 45, wherein said energizer unit transfers energy from said signals, as they are transmitted to said signal receiver, into electric energy.

49. The apparatus according to claim 48, further comprising an electric motor implanted in the patient for operating said adjustment device, said energizer unit comprising a rechargeable electric power supply for storing said electric energy and said control unit powers said electric motor with energy from said rechargeable electric power supply in response to signals received from said signal transmitter.

50. The apparatus according to claim 45, wherein said energizer unit comprises a battery, an electrically operable switch for connecting said battery to said signal receiver in an "on" mode when said switch is powered and to keep said battery disconnected from said signal receiver means in a "standby" mode when said switch is unpowered, and a rechargeable electric power supply for powering said switch.

51. The apparatus according to claim 50, wherein said control unit powers said electric motor with energy from said battery in response to signals received from said signal transmitter, when said switch is in its "on" mode.

52. The apparatus according to claim 45, further comprising an external energy transmitter for transmitting wireless energy, wherein said energizer unit comprises a battery and an operable switch for connecting said battery to said signal receiver in an "on" mode when said switch is powered and to keep said battery disconnected from said signal receiver in a "standby" mode when said switch is unpowered, said external energy transmitter for powering said switch.

53. The apparatus according to claim 52, wherein said energy transmitter directly powers said switch with said wireless energy to switch into said "on" mode.

54. The apparatus according to claim 45, wherein said energizer unit transfers said energy from said signals into direct or alternating current.

55. The apparatus according to claim 44, wherein said motor comprises an electric motor.

56. The apparatus according to claim 41, wherein said signal transmitter and signal receiver transmit and receive wave signals.

57. The apparatus according to claim 56, wherein said wave signals comprise electromagnetic waves, sound waves or carrier waves for remote control signals.

58. The apparatus according to claim 40, wherein said remote control comprises means for wireless transfer of energy from outside the patient's body to energy consuming components of said restriction device.

59. The apparatus according to claim 58, wherein said energy transferred by said means for transfer of energy comprises wave signals.

60. The apparatus according to claim 58, wherein said means for wireless transfer of energy directly powers said energy consuming components of said restriction device.

61. The apparatus according to claim 58, further comprising a motor adapted to be implanted in the patient for operating said adjustment device, wherein said means for wireless transfer of energy directly powers said motor with transferred energy.

62. The apparatus according to claim 40, wherein said remote control is capable of obtaining information on the size of the cross-sectional area of the food passageway when said restriction device is implanted in the patient and of commanding said adjustment device to adjust said restriction device in response to obtained information.

63. The apparatus according to claim 58, wherein said energy transferred by said means for transfer of energy comprises an electric or magnetic field.

64. The apparatus according to claim 40, wherein said remote control is capable of obtaining information from implantable parts of the apparatus and of commanding said adjustment device to adjust said restriction device in response to obtained information.

65. The apparatus according to claim 1, wherein said restriction device comprises at least two elements adapted to be positioned on different sides of the esophagus or stomach, and said adjustment device moves said elements toward each other to squeeze the esophagus or stomach between said elements to decrease the cross-sectional area in the esophagus or stomach and moves said elements away from each other to release the esophagus or stomach from said elements to increase the cross-sectional area.

66. The apparatus according to claim 1, wherein said restriction device comprises at least two articulated clamping elements adapted to be positioned on opposite or different sides of the esophagus or stomach, and said adjustment device turns said clamping elements toward each other to clamp the esophagus or stomach between said clamping elements to decrease the cross-sectional area in the esophagus or stomach, and turns said clamping elements away from each other to release the esophagus or stomach from said elements to increase the cross-sectional area in the esophagus or stomach.

67. The apparatus according to claim 1, wherein said restriction device is adapted to bend a portion of the esophagus or stomach.

68. The apparatus according to claim 67, wherein said restriction device comprises at least two bending members adapted to be positioned on opposite sides of the esophagus or stomach displaced relative to each other along the food passageway in the esophagus or stomach, and said adjustment device moves said bending members toward each other to bend the esophagus or stomach between said bending members to reduce the cross-sectional area in the esophagus or stomach, and moves said bending members away from each other to release the esophagus or stomach from said bending members to increase the cross-sectional area.

69. The apparatus according to claim 68, wherein said bending members comprise rollers.

70. The apparatus according to claim 1, wherein said restriction device is adapted to rotate a portion of the esophagus or stomach.

71. The apparatus according to claim 1, wherein said restriction device is adapted to control the cross-sectional area of the food passageway.

72. The apparatus according to claim 71, wherein said restriction device is operable to open and close the food passageway.

73. The apparatus according to claim 71, wherein said restriction device is adapted to steplessly control the cross-sectional area of the food passageway.

74. The apparatus according to claim 1, further comprising a pressure sensor for directly or indirectly sensing the pressure against the restriction device.

75. The apparatus according to claim 74, wherein said restriction device is controlled in response to signals from said pressure sensor.

76. The apparatus according to claim 1, further comprising an energy transfer device adapted to be implanted in the patient for transferring wireless energy directly or indirectly into kinetic energy for operation of said restriction device.

77. The apparatus according to claim 1, wherein said restriction device comprises a holding device adapted to prevent the region of the cardia from passing through the esophagal hiatus diaphragmatica, when said restriction device is implanted.

78. The apparatus according to claim 77, wherein said holding device comprises a support member.

79. The apparatus according to claim 1, wherein said post-operation adjustment device is adapted to non-invasively adjust said restriction device to change the size of the cross-sectional area.

80. The apparatus according to claim 1, further comprising a reversing device adapted be implanted in the patient, wherein said restriction device is capable of performing a reversible function and said reversing device reverses said reversible function.

81. The apparatus according to claim 1, further comprising an energy transmission device for transmitting wireless energy from outside the patient's body for energizing said adjustment device or other implantable components of the apparatus.

82. The apparatus according to claim 1, further comprising an accumulator or battery adapted to be implanted in the patient and adapted to be controlled from outside the patient's body to supply energy to said adjustment device or other implantable energy consuming components of the apparatus.

83. The apparatus according to claim 1, wherein said adjustment device adjusts said restriction device in a non-manual manner.

84. The apparatus according to claim 1, further comprising means for wireless transfer of energy from outside the patient's body to energy consuming implantable components of the apparatus including said operation device.

85. The apparatus according to claim 84, wherein said means for wireless transfer of energy directly powers said energy consuming implantable components of the apparatus including said operation device.

86. The apparatus according to claim 84, wherein said energy transferred by said means for transfer of energy comprises a wave signal.

87. The apparatus according to claim 84, wherein said energy transferred by said means for transfer of energy comprises an electric or magnetic field.

88. The apparatus according to claim 1, wherein said operation device is electrically powered.

89. A method for treating heartburn and reflux disease, comprising:
(a) surgically implanting in the abdomen of a patient suffering from heartburn and reflux disease an adjustable non-inflatable restriction device which forms a food passageway having a restricted cross-sectional area in the esophagus or in the stomach close to the cardia, and
(b) in a non-invasive procedure, mechanically adjusting the restriction device to change the size of the cross-sectional area of the food passageway.

90. A surgical method for laparoscopically implanting an adjustable restriction device of a heartburn and reflux disease treatment apparatus for forming a food passageway having a restricted cross-sectional area in the esophagus or stomach immediately close to the cardia, the method comprising:

(a) insufflating the abdomen of the patient to form a pneumoperitoneum;

(b) introducing at least one laparoscopic trocar into the abdomen;

(c) using a dissecting tool inserted through the laparoscopic trocar, dissecting the region of the esophagus or stomach adjacent or above the bursa omentalis;

(d) introducing the restriction device into the abdomen and applying the restriction device on the esophagus or stomach; and (e) post-operatively adjusting the restriction device in a non-invasive procedure to change the cross-sectional area of the food passageway.

91. A heartburn and reflux disease treatment apparatus, comprising:

an adjustable non-inflatable restriction device adapted to be implanted in a patient having heartburn and reflux disease to engage the esophagus or the stomach close to the cardia without forming an upper pouch of the stomach that substantially accumulates food to form a restricted food passageway in the stomach or esophagus, said restriction device being designed to work like an artificial sphincter to allow food to readily pass through the passageway and prevent regurgitation of stomach acids or foods into the patient's esophagus, and a holding device adapted to be implanted in the patient to hold the esophagus or stomach in a position where the left and right crus muscles are located, to prevent the region of the cardia from moving through the diaphragm muscle.

92. A heartburn and reflux disease treatment apparatus, comprising:

an adjustable non-inflatable restriction device adapted to be implanted in a patient having heartburn and reflux disease to engage the esophagus or the stomach close to the cardia without forming an upper pouch of the stomach that substantially accumulates food to form a restricted food passageway in the stomach or esophagus, and non-invasively activatable adjustment device to be implanted in the patient for mechanically adjusting said restriction device, to open the passageway to allow food to readily pass through the passageway and close the passageway to prevent regurgitation of stomach acids or foods into the patient's esophagus, when said restriction device engages the patient's stomach or esophagus.

93. The apparatus according to claim 92, wherein said adjustment device steplessly adjusts said restriction device.

* * * * *